US010138379B2

(12) United States Patent
Sun et al.

(10) Patent No.: US 10,138,379 B2
(45) Date of Patent: Nov. 27, 2018

(54) N-HALAMINES COMPOUNDS AS MULTIFUNCTIONAL ADDITIVES

(71) Applicant: Board of Regents, The University of Texas System, Austin, TX (US)

(72) Inventors: Yuyu Sun, Sioux Falls, SD (US); Zhaobin Chen, Shanghai (CN)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/580,540

(22) Filed: Dec. 23, 2014

(65) Prior Publication Data

US 2015/0166796 A1 Jun. 18, 2015

Related U.S. Application Data

(62) Division of application No. 11/502,892, filed on Aug. 11, 2006, now abandoned.

(60) Provisional application No. 60/707,331, filed on Aug. 11, 2005.

(51) Int. Cl.
| | |
|---|---|
| C09D 5/10 | (2006.01) |
| A01N 43/40 | (2006.01) |
| A01N 43/50 | (2006.01) |
| A01N 43/90 | (2006.01) |
| C09D 5/14 | (2006.01) |
| A01N 59/00 | (2006.01) |
| C02F 1/50 | (2006.01) |
| C02F 1/76 | (2006.01) |
| C02F 103/32 | (2006.01) |

(52) U.S. Cl.
CPC .............. *C09D 5/14* (2013.01); *A01N 43/40* (2013.01); *A01N 43/50* (2013.01); *A01N 43/90* (2013.01); *A01N 59/00* (2013.01); *C02F 1/50* (2013.01); *C02F 1/76* (2013.01); *C02F 2103/32* (2013.01); *C02F 2303/16* (2013.01); *C02F 2303/20* (2013.01)

(58) Field of Classification Search
None
See application file for complete search history.

(56) References Cited

U.S. PATENT DOCUMENTS

| | | | |
|---|---|---|---|
| 3,285,928 A | 11/1966 | Gubitz | |
| 3,488,701 A | 1/1970 | Herbes et al. | |
| 3,876,657 A | 4/1975 | Aelony et al. | |
| 3,971,757 A | 7/1976 | Rasberger | |
| 3,975,462 A | 8/1976 | Murayama et al. | |
| 4,091,223 A | 5/1978 | Zussman et al. | |
| 4,097,587 A | 6/1978 | Soma et al. | |
| 4,241,208 A | 12/1980 | Murayama et al. | |
| 4,677,130 A * | 6/1987 | Puzig | A01N 59/00 424/660 |
| 4,785,055 A | 11/1988 | Dexter et al. | |
| 4,931,562 A | 6/1990 | Akabane et al. | |
| 5,057,562 A | 10/1991 | Reinert | |
| 5,459,145 A | 10/1995 | Saccomano et al. | |
| 5,490,983 A | 2/1996 | Worley et al. | |
| 5,580,572 A | 12/1996 | Mikler et al. | |
| 5,670,646 A | 9/1997 | Worley et al. | |
| 5,705,545 A | 1/1998 | Avar et al. | |
| 5,714,127 A | 2/1998 | DeWitt et al. | |
| 5,817,806 A | 10/1998 | Rossi et al. | |
| 5,882,357 A | 3/1999 | Sun et al. | |
| 5,889,130 A * | 3/1999 | Worley | A01N 59/00 526/261 |
| 5,902,818 A | 5/1999 | Worley et al. | |
| 6,020,491 A | 2/2000 | Wonley et al. | |
| 6,077,319 A | 6/2000 | Sun et al. | |
| 6,162,452 A | 12/2000 | Worley et al. | |
| 6,241,783 B1 | 6/2001 | Sun | |
| 6,294,185 B1 | 9/2001 | Worley et al. | |
| 6,409,941 B1 | 6/2002 | Galbo et al. | |
| 6,482,756 B2 | 11/2002 | Li | |
| 6,576,154 B1 | 6/2003 | Li | |
| 6,585,989 B2 | 7/2003 | Herbst et al. | |
| 6,670,412 B1 | 12/2003 | Ederly et al. | |
| 6,746,154 B2 | 6/2004 | Greene et al. | |

(Continued)

FOREIGN PATENT DOCUMENTS

| | | |
|---|---|---|
| DE | 1900169 | 9/1969 |
| DE | 2437916 | 2/1976 |

(Continued)

OTHER PUBLICATIONS

Kruczala, et al., "Thermal Aging of Heterophasic Propylene-Ethylene Copolymers: Morphological Aspects Based on ESR, FTIR, and DSC," Macromolecules (2003), 36:1899-1908.

Kruczala, et al., "Thermal Aging of Heterophasic Propylene-Ethylene Copolymers: Spatial and Temporal Aspects of Degradation Based on ESR, ESR Imaging, and FTIR," Macromolecules (2003), 36:1909-1919.

Larson, et al., "Inactivation of Bacillus subtilis spores with ozone and monochloramine," Water Research (2003), 37:833-844.

Lee, et al., "Antibacterial effect of nanosized silver colloidal solution on textile fabrics," J Mater Sci (2003), 38:2199-2204.

Lee, et al., "Permanent, Nonleaching Antibacterial Surfaces. 1. Synthesis by Atom Transfer Radical Polymerization," Biomacromolecules, (2004), 5:877-882.

Lin, et al., "Antimicrobial Treatment of Nylon," J Appl Polym Sci (2001), 81:943-947.

(Continued)

*Primary Examiner* — Susan T Tran
*Assistant Examiner* — William Craigo
(74) *Attorney, Agent, or Firm* — Meunier Carlin & Curfman LLC

(57) ABSTRACT

The present invention is a composition and method for making and using a rechargeable multifunctional additive that reduce the formation of biofilms on a surface, the additive can also remain photo and thermally stable by synthesizing one or more N-halamine compounds and adding one or more N-halamine biocidal compounds to a target material prior, during or after the target material is made. The resultant material can be used directly to provide antimicrobial functions and control biofilm formation, or the material can be further processed into an article.

8 Claims, 15 Drawing Sheets

(56) References Cited

U.S. PATENT DOCUMENTS

| | | | |
|---|---|---|---|
| 6,762,225 | B2 | 7/2004 | Malik et al. |
| 6,768,009 | B1 | 7/2004 | Sun et al. |
| 6,770,287 | B1 | 8/2004 | Sun et al. |
| 6,878,761 | B2 | 4/2005 | Gugumus |
| 6,969,769 | B2 | 11/2005 | Worley et al. |
| 7,084,208 | B2 | 8/2006 | Sun et al. |
| 7,335,373 | B2 | 2/2008 | Worley et al. |
| 7,358,373 | B2 | 4/2008 | Bamberg et al. |
| 7,541,398 | B2 | 6/2009 | Sun et al. |
| 8,211,361 | B2 | 7/2012 | Sun et al. |
| 8,367,823 | B2 | 2/2013 | Sun et al. |
| 8,486,428 | B2 | 7/2013 | Sun et al. |
| 2002/0123281 | A1 | 9/2002 | Wu |
| 2003/0056297 | A1 | 3/2003 | Sun |
| 2003/0064645 | A1 | 4/2003 | Worley et al. |
| 2003/0143187 | A1 | 7/2003 | Worley et al. |
| 2003/0216581 | A1* | 11/2003 | Sun .................. A01N 43/50 548/263.2 |
| 2004/0063831 | A1 | 4/2004 | Sheppard et al. |
| 2004/0086480 | A1 | 5/2004 | Worley et al. |
| 2004/0121681 | A1 | 6/2004 | Lindsay et al. |
| 2004/0127667 | A1 | 7/2004 | Worley et al. |
| 2004/0191315 | A1 | 9/2004 | Slattery et al. |
| 2004/0265565 | A1 | 12/2004 | Fischer et al. |
| 2004/0266918 | A1 | 12/2004 | Balliello et al. |
| 2005/0186173 | A1 | 8/2005 | Worley et al. |
| 2006/0148940 | A1 | 7/2006 | Sun et al. |
| 2007/0062884 | A1 | 3/2007 | Sun et al. |
| 2007/0086976 | A1 | 4/2007 | Sun et al. |
| 2007/0092724 | A1 | 4/2007 | Li et al. |
| 2008/0268189 | A1 | 10/2008 | Sun et al. |

FOREIGN PATENT DOCUMENTS

| | | | |
|---|---|---|---|
| DE | 2437917 | | 2/1976 |
| EP | 0240370 | A | 10/1987 |
| GB | 1211521 | | 11/1970 |
| WO | 199420118 | | 9/1994 |
| WO | 199608949 | | 3/1996 |
| WO | 199810648 | | 3/1998 |
| WO | 2001007550 | A1 | 2/2001 |
| WO | 2001072715 | | 10/2001 |
| WO | 2002006579 | A2 | 1/2002 |
| WO | 2002030477 | | 4/2002 |
| WO | 2005058814 | A2 | 6/2005 |
| WO | 2006074455 | | 7/2006 |
| WO | 2007126775 | | 11/2007 |
| WO | 2009039180 | | 3/2009 |

OTHER PUBLICATIONS

Lin, et al., "Infrared characterization of biocidal nylon." Polymer (2001), 42:7903-7906.

Linger, et al., "Evaluation of a hydrogen peroxide disinfectant for dental unit waterlines." J Am Dent Assoc (2001),132:1287-1291.

Lister, Joseph "On the Antiseptic Principle in the Practice of Surgery" Lancet 1867, 2, 353.

Luo, et al., "Acyclic N-halamine-based fibrous materials: preparation, characterization, and biocidal functions." J Polym Sci: Part A Polym Chem (2006),44:3588-3600.

Mills, S.E., "The dental unit waterline controversy: defusing the myths, defining the solutions." J Am Dent Assoc (2000),131:1427-1441.

Motyakin, et al., "Electron Spin Resonance Imaging and ATR-FTIR Study of Poly(acrylonitrile-butadiene-styrene) Containing a Hindered Amine Stabilizer and Thermally Treated at 353 K," Macromolecules (2002), 35:3984-3992.

Motyakin, et al., "Spectral Profiling by 1D and 2D Electron Spin Resonance Imaging: Nitroxide Radicals in UV and Thermal Degradation of Poly(acrylonitrile-butadiene-styrene) Containing a Hindered Amine Stabilizer," Macromolecules (2001), 34:2854-2864.

Muzzarelli, et al., "Fungistatic Activity of Modified Chitosans against Saprolegnia parasitica," Biomacromolecules, (2001); 2:165-169.

Neely, et al. "Survival of Enterococci and Staphylococci on Hospital Fabrics and Plastic," J Clin Microbiol (2000), 38:724-726.

Neely, et al., "Survival of Some Medically Important Fungi on Hospital Fabrics and Plastics," J Clin Microbiol (2001), 39:3360-3361.

Neely, Alice N. "A Survey of Gram-Negative Bacteria Survival on Hospital Fabrics and Plastics" J. Burn. Care. Rehabil. 2000, 21, 523-527.

Nishimoto, et al. "Radiation-induced structural changes in poly-(propylene-ran-ethylene) film: Effect of antioxidant 2,2,6,6-tetramethylpiperidine derivatives" (1992), 39(5); 413-419.

Oliphant, et al. "Fever in Laundry Workers, Presumable Transmitted From Contaminated Clothing" R. R. Am. J. Hyg. 1949, 47, 76-82.

Orr, et al. "Therapeutic beds: the Trojan horses of the 1990s?" Lancet 1994, 344, 65-66.

Ozcan, et al. "The effect of disinfectant agents in eliminating the contamination of dental unit water." J Oral Rehabili (2003),30:290-294.

Phaneuf, et al. "Application of the quinolone antibiotic ciprofloxacin to Dacron utilizing textile dyeing technology" . J. Biomed. Mater. Res. 1993, 27, 233-237.

Qian, et al., "Durable and Regenerable Antimicrobial Textiles: Improving Efficacy and Durability of Biocidal Functions," J Appl Polym Sci (2004), 91:2588-2593.

Rabea, et al., "Chitosan as Antimicrobial Agent: Applications and Mode of Action," Biomacromolecules, (2003), 4:1457-1465.

Ramage, et al., "Formation of Propionibacterium acnes biofilms on orthopaedic biomaterials and their susceptibility to antimicrobials." Biomaterials (2003),24:3221-3227.

Richmond, et al. "Biosafety in Microbiological and Biomedical Laboratories", 4th ed.; U.S. Government printing office: Washington, DC, 1999.

Roberts, et al., "Dental unit waterline antimicrobial agent: effect on dentin bond strength." J Am Dent Assoc (2000),131:179-183.

Setnescu, et al., "Chemiluminescence study on the oxidation of several polyolefins—I. Thermal-induced degradation of additive-free polyolefins," Polym. Degrad. Stab. (1998), 60:377-383.

Sidwell, et al. "Quantitative Studies on Fabrics as Disseminators of Viruses—I. Persistence of Vaccinia Virus on Cotton and Wool Fabrics" Appl. Microbiol. 1966, 14, 55-59.

Sidwell, et al. "Quantitative Studies on Fabrics as Disseminators of Viruses—III. Persistence of Vaccinia Virus on Fabrics Impregnated with a Virucidal Agent" Appl. Microbiol. 1967, 15, 921-927.

Sidwell, et al. "Quantitative Studies on Fabrics as Disseminators of Viruses—IV. Virus Transmission by Dry Contact of Fabrics" Appl. Microbiol. 1970, 19, 950.

Sidwell, et al. "Quantitative Studies on Fabrics as Disseminators of Viruses—V. Effect of Laundering on Poliovirus-Contaminated Fabrics" Appl. Microbiol. 1971, 21, 227-234.

Standaert, et al. "Nosocomial Transmission of *Salmonella* Gastroenteritis to Laundry Workers in a Nursing Home" Infect. Control Hosp. Epidemiol. 1994, 15, 22-26.

Suffis, et al. "Spectrophotometric Determination of a p-Phenylenediamines and p-Aminophenols with Nihndrin" Analytical Chemistry, vol. 36, No. 3, Mar. 1964, pp. 636-637.

Sun, et al., "Durable and Regenerable Antibacterial Finishing of Fabrics with a New Hydantoin Derivative," Ind Eng Chem Res (2001), 40:1016-1021.

Sun, et al., "Durable and Regenerable Antimicrobial Textile Materials Prepared by a Continuous Grafting Process," J Appl Polym Sci (2002), 84:1592-1599.

Sun, et al., "Novel Refreshable N-Halamine Polymeric Biocides Containing Imidazolidin-4-one Derivatives," J Polym Sci Part A Polym Chem (2001), 39:3073-3084.

Sun, et al., "Novel Refreshable N-Halamine Polymeric Biocides: N-Chlorination of Aromatic Polyamides," Ind Eng Chem Res (2004), 43:5015-5020.

(56) References Cited

OTHER PUBLICATIONS

Sun, et al., "Novel Refreshable N-Halamine Polymeric Biocides: Grafting Hydantoin-Containing Monomers onto High Performance Fibers by a Continuous Process," J. Appl. Polym. Sci. (2003), 88:1032-1039.

Sun, et al., "Synthesis, Characterization, and Antibacterial Activities of Novel N-Halamine Polymer Beads Prepared by Suspension Copolymerization," Macromolecules (2002), 35:8909-8912.

Sykes, G. "The Sporicidal Properties of Chemical Disinfectants" J. Appl. Bact. 1970, 33, 147-156.

Tao, et al., "Surface functionalized polypropylene: Synthesis, characterization, and adhesion properties." Macromolecules (2001),34:7672-7679.

Tennen, et al., "Mechanisms of killing of spores of Bacillus subtilis by iodine, glutaraldehyde and nitrous acid," J Appl Microbiol (2000), 89:330-338.

Tew, et al., "De novo design of biomimetic antimicrobial polymers," Proc. Natl. Acad. Sci. USA. (2002), 99:5110-5114.

Tiller, et al., "Designing Surfaces that Kill Bacteria on Contact," Proc. Natl. Acad. Sci. USA. (2001), 98:5981-5985.

Walker, et al., "Microbiological evaluation of a range of disinfectant products to control mixed-species biofilm contamination in a laboratory model of a dental unit water system." Appl Environ Microbiol (2003),69:3327-3332.

Worley, et al. "A Novel N-Halamine Monomer for Preparing Biocidal Polyurethan Coatings" Air Force Research Laboratory, Mar. 2002.

Yorganci, et al., "Activity of antibacterial impregnated central venous catheters against Klebsiella pneumoniae." Intensive Care Med (2002),28:438-442.

Aggarwal, et al., "Development of an infection-resistant bifunctionalized Dacron biomateria," J Biomed Mater Res (published online Aug. 2, 2005), 75A:224-231.

Albert, et al., "Structure-Activity Relationships of Oligoguanidines—Influence of Counterion, Diamine, and Average Molecular Weight on Biocidal Activies," Biomacromolecules, (2003), 4:1811-1817.

Amornsakchai, et al. "Surface modification of low density polyethylene using accelerated decomposition of potassium persulfate and ceric ion induced acrylamide grafting." J Mater Sci Lett (2002), 21:1035-1038.

Appendini, et al., "Review of antimicrobial food packaging," Innov. Food Sci. Emerg. Tech. (2002), 3:113-126.

Bamford, et al. "Studies in polymer surface functionalization and grafting for biomedical and other applications" Polymer 1994, 35, 2844-2852.

Barker, et al., Effects of cleaning and disinfection in reducing the spread of Norovirus contamination via environmental surfaces, J Hosp Infect (Available online Aug. 3, 2004), 58:42-49.

Binder, et al., "Emerging Infectious Diseases: Public Health Issues for the 21st Century," Science (May 21, 1999), 284:1311-1313.

Bloomfield, et al. "Effect of chlorine-releasing agents on Bacillus subtilis vegatative cells and spores" Lett. Appl. Microbiol. 1989, 8, 101-104.

Braun, et al., "Antimicrobial Polymers Containing Melamine Derivatives. I. Preparation and Characterization of Chloromelamine-Based Cellulose," Polym. Sci., Part A: Polym. Chem. (2004), 42:3818-3827.

Cen, et al., "Antibacterial activity of cloth functionalized with Nalkylated poly(4-vinylpyridine)," J Biomed Mater Res (Published online Aug. 9, 2004), 71A:70-80.

Chen, et al., "Quaternary Ammonium Functionalized Poly(propylene imine) Dendrimers as Effective Antimicrobials: Structure-Activity Studies," Biomacromolecules, (Published online Aug. 1, 2000), 1:473-480.

Chen, et al., "N-Chloro-Hindered Amines as Multifunctional Polymer Additives," Macromolecules (Published online Aug. 17, 2005), 38:8116-8119.

Dart, et al. "Retention of Aspergillus Niger Spores on Textiles" ASTM Special Technical Publication 2000, STP 1386 (7), 251-268.

Datta, et al. "An Outbreak of infection with *Salmonella typhimuium* in a general hospital" J. Hyg. Camb. 1960, 58, 229-214.

Depaola, et al. "A review of the science regarding dental unit waterlines." J Am Dent Assoc (2002),133:1199-1206.

Dhamodharan, et al., "Investigation of the mercat reaction as a tool for the introduction of nitrogen surface functionality on linear low-density polyethylene (LLDPE) and polypropylene (PP)." Langmuir (2001),17:3368-3374.

Dixon, et al. "Quantitative Studies on Fabrics as Disseminators of Viruses" Appl. Microbiol. 1966, 14, No. 2, 183-188.

Eknoian, et al., "Novel Antimicrobial N-halamine polymer coatings generated by emulsion polymerization," Polymer (1999), 40:1367-1371.

Eknoian, et al., "Monomeric and Polymeric N-Halamine Disinfectants," Ind. Eng. Chem. Res. (Published online Jun. 2, 1998), 37:2873-2877.

George, et al. "Poly(N-bromoacrylamide): A New Polymeric Recyclable Oxidizing and Brominating Reagent" Macromolecules 1988, 21, 1867-1870.

Gorman, et al., "The concomitant development of poly(vinyl chloride)-related biofilm and antimicrobial resistance in relation to ventilator-associated pneumonia." Biomaterials (2001),22:2741-2747.

Haas, et al. "Imidization Reaction in Polyvinylamides" J. Polym. Sci. Part A Polym. Chem. 1971, 9, 3583-3593.

Hahn, et al., "Chlorination of Substituted Polyacrylamides," Die Angewandte Makromolekulare Chemie (1976), 50:53-65.

Hall-Stoodley, et al., "Bacterial biofilms: from the natural environment to infectious diseases." Nature Rev Microbiol (Feb. 2004),2:95-108.

Hardy, et al. "The Formation and Hydrolysis of Substituted N-Chloro-N-methylbenzamides in Aqueous Alkali", P. J. Chem. Soc. B. 1967, 1151-1154.

European Patent Office (ISA), International Search Report for PCT/US2001/09071 dated Jul. 18, 2002.

United States Patent & Trademark Office (ISA), International Search Report for PCT/US2006/00849 dated Jul. 18, 2002.

United States Patent & Trademark Office (ISA), International Search Report and Written Opinion for PCT/US2007/007506 dated Jul. 25, 2008.

Korean Intellectual Property Office (ISA), International Search Report and Written Opinion for PCT/US2008/076687 dated Apr. 3, 2009.

Jansson, et al., "Degradation of post-consumer polypropylene materials exposed to simulated recycling—mechanical properties," Polym. Degrad. Stab. (2003), 82:37-46.

* cited by examiner

Formula 1A

Formula 2B

Formula 3C

Formula 4D

Formula 5E

Formula 6F

Formula 7G

Formula 8H

Pure PP films

PP films containing 0.5wt% of BTMP

PP films containing 0.5wt% of Cl-BTMP ial compounds that act as multifunctional materials, as an example.

N-HALAMINES COMPOUNDS AS MULTIFUNCTIONAL ADDITIVES

CROSS-REFERENCE TO RELATED APPLICATIONS

This application is a divisional patent application of U.S. Ser. No. 11/502,892 filed on Aug. 11, 2006 which claims priority to U.S. Provisional Application Ser. No. 60/707,331, filed Aug. 11, 2005, the contents of which are incorporated by reference herein in their entirety.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISC

Not applicable.

TECHNICAL FIELD OF THE INVENTION

The present invention relates in general to the field of multifunctional additives of materials, and more particularly, to the chemically N-halamines as additives of material to provide antimicrobial, anti-biofilm, and/or photo and thermal stabilities.

BACKGROUND OF THE INVENTION

Without limiting the scope of the invention, its background is described in connection with additive compounds that act as multifunctional materials, as an example.

Contamination of materials by microorganisms such as pathogenic bacteria, molds, fungi and viruses is of great concern in the medical industry, the food and restaurant industries, as well as in consumer products as a result of the potential for the spread of infections. Survival of microorganisms on various materials and transfer of these microorganisms between materials, animals and humans has been demonstrated, and it is widely accepted that microorganism-contaminated materials can be elements in cross-infections and transmission of diseases caused by microorganisms. Furthermore, the structure and characteristics of biofilms allow the growth and proliferation of contaminants and make the cleaning and removal of pathogenic bacteria, molds, fungi and viruses extremely difficult.

Microorganisms have strong abilities to survive on ordinary materials and can stay alive for as long as 90 days. These microorganisms can further develop into firmly attached biofilms. A biofilm is an accumulation of microorganisms (e.g., bacteria, fungi, and/or protozoa, with associated bacteriophages and other viruses) embedded in a polysaccharide matrix and adherent to solid biologic or non-biologic surface.

Biofilms are remarkably difficult to treat with antimicrobials, which may be readily inactivated or fail to penetrate into the biofilm. In addition, microorganisms within biofilms have increased (e.g., up to 1000-fold higher) resistance to antimicrobial compounds, even though these same microorganisms are sensitive to these agents if grown under planktonic conditions. Furthermore, microorganisms express new, and sometimes more virulent phenotypes when grown within a biofilm. Such phenotypes may not have been detected in the past because the organisms were grown on rich nutrient media under planktonic conditions. The growth conditions are quite different particularly in the depths of biofilms, where nutrients and oxygen are usually limited, and waste products from neighbors can be toxic. In short, microorganisms found at the bottom of the biofilm look and act different from microorganisms located at the surface.

Biofilms represent a serious problem in environmental, medical and industrial fields. Additionally, biofilms increase the opportunity for gene transfer between/among microorganisms allowing microorganisms resistant to antimicrobials or chemical biocides to transfer the genes for resistance to neighboring susceptible microorganisms. Gene transfer can convert a previous avirulent commensal organism into a highly virulent pathogen. Certain species of microorganisms communicate with each other within the biofilm. As their density increases, the organisms secrete low molecular weight molecules that signal when the population has reached a critical threshold, e.g., quorum sensing, is responsible for the expression of virulence factors.

Microorganisms embedded within biofilms are resistant to both immunological and non-specific defense mechanisms of the body. Contact with a solid surface triggers the expression of a panel of bacterial enzymes, which catalyze the formation of sticky polysaccharides that promote colonization and protection. The structure of biofilms is such that immune responses may be directed only at those antigens found on the outer surface of the biofilm, and antibodies and other serum or salivary proteins often fail to penetrate into the biofilm. In addition, phagocytes are unable to effectively engulf a bacterium growing within a complex polysaccharide matrix attached to a solid surface. This causes the phagocyte to release large amounts of pro-inflammatory enzymes and cytokines, leading to inflammation and destruction of nearby tissues. Because biofilm formation is triggered by the survival and adherence of microbes onto different materials, the introduction of biocidal functions into the target materials can be an effective method to inactivate the microbes and thus control biofilms.

In addition to the medical and healthcare fields, the food and restaurant industries, as well as in consumer are increasingly concerned with microbial contamination, e.g., food contact between contaminated articles. Multiple outbreaks of food borne bacterium such as $E.\ coli$, have made people increasingly conscious of methods to control the spread of such bacterium. Food contact materials such as cutting boards, sponges, towels and the like have long been suspected to be vectors for the spread of food borne microorganisms. Therefore, the induction of biocidal properties should be an effective feature of healthcare and hygienic-use applications.

The foregoing problems have been recognized for many years and while numerous solutions have been proposed, none of them adequately address all of the problems in a single device, e.g., effectiveness against many forms of bacteria, toxicity, stability and rechargeability.

SUMMARY OF THE INVENTION

The present inventors recognized a need for rechargeable additives that act as broad-spectrum antimicrobial and biofilm-controlling agents, which may also provide other desirable functions, such as photo and thermal stabilization, reducing leaching of organic contaminants into the medium to be disinfected and maintaining a low concentration of free halogen in the medium.

The present invention uses N-halamine-based compounds to provide biocidal and biofilm-controlling functions. An N-halamine is a compound containing one or more nitrogen-halogen covalent bonds that is normally formed by the chlorination or bormination of cyclic imide, amide or amine groups. One of the properties of N-halamines is that when microbes come into contact with the N—X structures (e.g., X is Cl or Br), a halogen exchange reaction occurs, resulting in the expiration of the microorganisms. The process consumes halogens, but the consumed halogens can be recharged by another halogen treatment. Thus, N-halamines are generally regarded as rechargeable batteries of covalently bound halogens. N-halamines are much more stable and safer to use than hypochlorite bleach, yet have a similar antimicrobial efficacy. In the current invention, imide-, amide-, melamine- and amine-based N-halamines or their combinations are used as the additives.

The present invention provides a method of making a rechargeable antimicrobial and biofilm-controlling material by synthesizing one or more N-halamine biocidal compounds and adding one or more N-halamine biocidal compounds to a target material. The target material is used directly, or processed into the desired articles, coatings, paints, medical devices and so forth.

The present invention also provides a method of making an antimicrobial and biofilm-controlling material by adding one or more precursors of the N-halamine biocidal compounds to a target materials and/or processing one the target material into an article. Then one or more halogen sources are added to the material or article, wherein the one or more precursors of the N-halamine biocidal compounds are transformed into one or more active N-halamine biocidal compounds.

The present invention provides a method of reducing the formation of biofilms on a surface by synthesizing one or more N-halamine biocidal compounds and adding the one or more N-halamine biocidal compounds to a target material. The target material having one or more N-halamine biocidal compounds is then placed into contact with the surface, whereby the formation of biofilms is reduced.

The present invention includes a self-decontaminating monomeric or polymeric N-halamine biocidal composition having the formula I, II, III, IV, V, VI, VII, VIII or combinations thereof, wherein X, $X^1$, $X^2$, $X^3$ and $X^4$ are individually a Hydrogen or a halogen; $R^1$ to $R^{10}$ are independently hydrogens, halogens, one or more $C_1$ to $C_{40}$ alkyl, $C_1$ to $C_{40}$ alkylene, $C_1$ to $C_{40}$ alkenyl, $C_1$ to $C_{40}$ alkynyl, $C_1$ to $C_{40}$ aryl, $C_1$ to $C_{30}$ alkoxy, $C_1$ to $C_{40}$ alkylcarbonyl, $C_1$ to $C_{40}$ alkylcarboxyl, $C_1$ to $C_{40}$ amido, $C_1$ to $C_{40}$ carboxyl, or combinations thereof.

For example, the present invention provides a rechargeable N-halamine biocidal compound including 3-substituted-1-N-halo-5,5-disubstituted-hydantoin; 3,3'-bissubstituted-1,1'-N-halo-5,5,5'5'-substituted-2,2',4,4'-imidazolidinedione; 1,3,8-Triaza-3-substituted-7,7,9,9-substituted-1,8-N-halo-2,4-dioxospiro[4.5]decane; 3,3'-disubstituted-bis(7,7,9,9-substituted)-1,3,8-Triazaspiro[4.5]decane-1,1',8,8'N-halo-2,4-dione; 8,8'-disubstituted-bis(7,7,9,9-substituted)-1,3,8-Triazaspiro[4.5]decane-1,1',3,3'N-halo-2,4-dione; poly(vinyl chloride-co-3-vinyl-N-halo-5,5-disubstituted hydantoin); poly(vinylchloride-co-3-vinyl-1,3,8-Triaza-7,7,9,9-substituted-1,8-N-halo-2,4-dioxospiro[4.5]decane).

Furthermore, biofilm controlling materials which are stable to photo and thermal treatment may be made by mixing a sterically hindered amine light stabilizer with a source of halide atoms to form a sterically hindered N-halo-amine and forming a material in the presence of the sterically hindered N-halo-amine.

The present invention also includes a method of recharging a biofilm-controlling material, which are stable to photo and thermal challenge by exposing a sterically hindered amine stabilizer to a source of halide atoms.

The present invention includes a method of making a biofilm controlling material which is photo and thermal treatment stable by forming an N-halamine biocidal compound which is added to one or more halogen sources, wherein the N-halamine biocidal compound is transformed into one or more active N-halamine biocidal compounds.

Another example of the present invention includes a hindered N-halo-amine, which can provide biofilm-controlling as well as photo and thermal stabilizing functions. Examples of these hindered N-halo-amines include, but not limit to, Bis(N—X-2,2,6,6-tetramethyl-4-piperidyl)sebacate; Poly[[6-[(1,1,3,3-tetramethylbutyl)amino]-s-triazine-2,4-diyl]-N—X-[(2,2,6,6-tetramethyl-4-piperidyl)imino]-hexamethylene-[(2,2,6,6-tetramethyl-4-piperidylimino]]; N—X-[(4-piperidyl)alkyl formate]; Poly[(6-morpholino-s-triazine-2,4-diyl)-N—X-[2,2,6,6-tetramethyl-4-piperidyl] imino]-hexamethylene[(2,2,6,6-tetramethyl-4-piperidyl) imino]]; 3-Dodecyl-N-chloro-(2,2,6,6-tetramethyl-4-piperidinyl)succinimide; 2,2,4,4-Tetramethyl-N—X-7-oxa-3,20-diazadispiro[5.1.11.2]-heneicosan-21-one; D-Glucitol, 1,3:2,4-bis-O—(N-chloro-2,2,6,6-tetramethyl-4-piperidinylidene); 1,1'-ethylenebis(N—X-3,3,5,5-tetramethyl-piperazinone); N—X-2,2,4,4-tetramethyl-7-oxa-20-(oxiranylmethyl)-3,20-diazadispiro[5.1.11.2]henicosan-21-one; 1,2,3,4-Butanetetracarboxylic acid, polymer with β,β,β',β'-tetramethyl-2,4,8,10-tetraoxaspiro[5.5]undecane-3,9-diethanol, N—X-2,2,6,6-tetramethyl-4-piperidinyl ester; Poly[oxy[methyl[3-[N—X-(2,2,6,6-tetramethyl4-piperidinyl)-oxy]propyl]silylene]]; 1,1',1"-[1,3,5-Triazine-2,4-6-triyltris[(cyclohexylimino)ethylene]]tris(N-chloro-3,3,5,5-tetramethyl-piperazinone); and mixtures and combinations thereof, wherein X is Cl, Br or combinations thereof.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
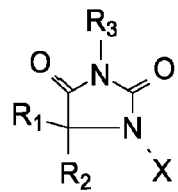
FIG. 1 is a schematic of general chemical structures of the N-halamine compounds.
Figure 1:
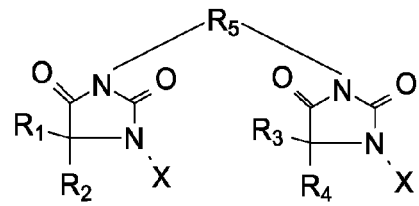
Figure 1:
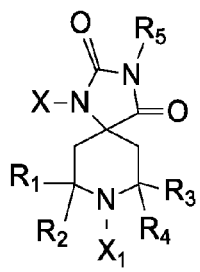
Figure 1:
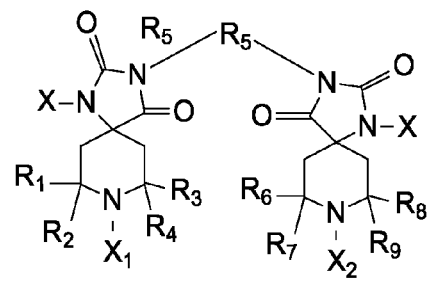
Figure 1:
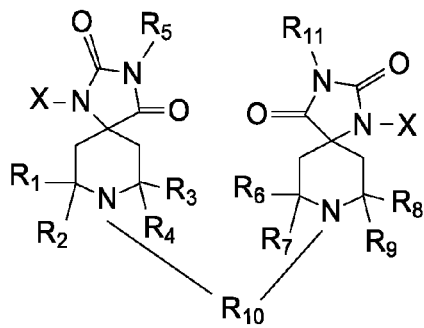
Figure 1:
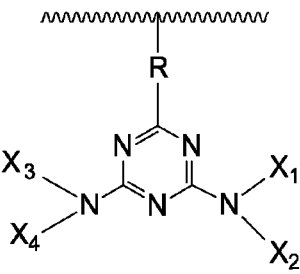
Figure 1:
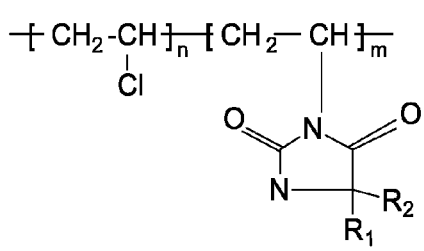
Figure 1:
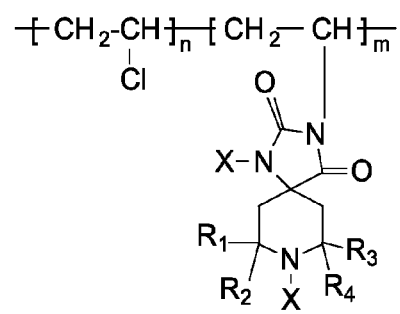

While the making and using of various embodiments of the present invention are discussed in detail below, it should be appreciated that the present invention provides many applicable inventive concepts that can be embodied in a wide variety of specific contexts. The terminology used and specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The terms "antimicrobial compound," "antimicrobial," "microbicidal," "biocide," "biocidal" and "halogenated amide antimicrobial" are used interchangeably herein and refer to halogenated amides that function as biocides to kill at least some types of microorganisms, or to inhibit the growth or reproduction of at least some types of microorganisms (i.e., compounds which inhibit the growth of, or kills, microorganisms such as bacteria, molds, slimes, fungi, etc.).

As used herein, the term "alkyl" denotes branched or unbranched hydrocarbon chains, preferably having about 1 to about 10 carbons, such as, methyl, ethyl, n-propyl, iso-propyl, n-butyl, sec-butyl, iso-butyl, tert-butyl, octadecyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

The term "alkylene" refers to a divalent alkyl group as defined above, such as methylene ($-CH_2-$), propylene ($-CH_2CH_2CH_2-$), chloroethylene ($-CHClCH_2-$), 2-thiobutene $-CH_2CH(SH)CH_2CH_2$, 1-bromo-3-hydroxyl-4-methylpentene ($-CHBrCH_2CH(OH)CH(CH_3)CH_2-$), and the like.

As used herein, the term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

As used herein, the term "aryl" denotes a chain of carbon atoms which form at least one aromatic ring having between about 4-14 carbon atoms, such as phenyl, naphthyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "alkoxy" denotes —OR—, wherein R is alkyl. The term "alkylcarbonyl" denote an alkyl group as defined above substituted with a C(O) group, for example, $CH_3C(O)-$, $CH_3CH_2C(O)-$, etc. As used herein, the term "alkylcarboxyl" denote an alkyl group as defined above substituted with a C(O)O group, for example, $CH_3C(O)O-$, $CH_3CH_2C(O)O-$, etc. As used herein, the term "amido" denotes an amide linkage: —C(O)NHR (wherein R is hydrogen or alkyl). The term "amino" denotes an amine linkage: —NR—, wherein R is hydrogen or alkyl. The term "carbocycle" means a cyclic hydrocarbon chain having about 5 to about 8 ring carbons such as cyclopentyl, cylcohexyl, etc. These groups can be optionally substituted with one or more functional groups as defined under "alkyl" above.

As used herein, the term "carboxyl" denotes —C(O)O—, and the term "carbonyl" denotes —C(O)—. The term "cycloalkyl" signifies a saturated, cyclic hydrocarbon group with 3-8, preferably 3-6 carbon atoms, i.e. cyclopropyl, cyclobutyl, cyclopentyl and cyclohexyl and the like.

As used herein, the terms "N-halamines," "Heterocyclic N-halamine" and "cyclic N-halamine unit" denotes a class of chemicals that contain a halogen bound to a nitrogen atom, where the nitrogen is a member of a ring, along with carbon atoms. When bound to the nitrogen, the halogen is in a stable form and retains the ability to interact with targets on the surfaces of bacteria and other microbes. The presence of the halogen renders it biocidal. For example, heterocyclic, monocyclic compounds having 4 to 7-membered ring, wherein at least 3 members of the ring are carbon, and from 1 to 3 members of the ring are nitrogen heteroatom, and from 0 to 1 member of the ring is oxygen heteroatom. Additionally, there may be from 0 to 2 carbon members comprise a carbonyl group, and wherein at least 1 to 3 nitrogen atoms are substituted with a hydroxyalkyl group, such as $-CH_2OH$, or an alkoxyalkyl group, such as $-CH_2OCH_3$. In addition, the ring members can be further substituted with alkyl groups, such as methyl, ethyl, etc.

The term "halogen" includes chlorine, fluorine, bromine and mixtures thereof. The term "heteroaryl" refers to an aromatic mono- or bicyclic radical having 5 to 10, preferably 5 to 6 ring atoms, containing one to three heteroatoms, preferably one heteroatom, e.g. independently selected from nitrogen, oxygen or sulfur. Examples of heteroaryl groups are thiophenyl, isoxazolyl, thiazolyl, piperidinyl, pyridinyl, pyrrolyl, imidazolyl, tetrazolyl, preferably pyridinyl, isoxazolyl or thiazolyl. Optionally, the heteroaryl group can be mono-, di- or tri-substituted, independently, with phenyl, alkyl, alkylcarbonyl, alkoxycarbonyl, hydroxy, amino, alkylamino, dialkylamino, carboxy, alkoxycarbonylalkyl, preferably alkyl.

The term "heterocycle" means a straight chain or ring system that may contain from zero to four heteroatoms selected from N, O and S, wherein the nitrogen and sulfur atoms are optionally oxidized, and the nitrogen atom(s) are optionally quaternized. These groups can be optionally substituted with one or more functional groups as defined under "alkyl" above.

As used herein, the terms, "polymer" and "copolymer" are at times used interchangeably to mean a cyclic amine or N-halamine unit joined by a linkage to a second cyclic amine or N-halamine unit is not meant to be limiting as to the number of cyclic amine or N-halamine units in a polymer, e.g., two or more cyclic amine or N-halamine units, and the number of units in any given polymer can vary according to the use intended for the polymer. Other polymers include flexible PVC, polyurethanes, polyolefins, thermoplastic polyolefins, thermoplastic elastomers, rubber, silicones, polyester; however the skilled artisan will recognize other polymers may be used. The polymer may be a random copolymer contains a random arrangement of the multiple monomers. The polymer may be a block copolymer contains blocks of monomers of the same type. The polymer may also be a graft copolymer contains a main chain polymer consisting of one type of monomer with branches made up of other monomers. For example, the polymer can comprise 2, 3, 4, 5, 6, 7, 8, 9, 10, 20, 25, 30, 40, 50, 75, 100, 150, 200, 250, 500, 1000, and so forth, units.

The present invention provides a method of making a rechargeable antimicrobial and biofilm-controlling material by synthesizing one or more N-halamine biocidal compounds and adding one or more N-halamine biocidal compounds to a target material. The target material is used directly, or processed into the desired articles, coatings, paints, medical devices and so forth.

The present invention also provides a method of making an antimicrobial and biofilm-controlling material by adding one or more precursors of the N-halamine biocidal compounds to a target materials and/or processing one the target material into an article. Then one or more halogen sources are added to the material or article, wherein the one or more precursors of the N-halamine biocidal compounds are transformed into one or more active N-halamine biocidal compounds.

Generally, the one or more N-halamine biocidal compounds include one or more 4 to 7 membered rings and one or more nitrogen heteroatoms. Specific examples include comprises 3-substituted-1-N-halo-5,5-disubstituted-hydantoin; 3,3'-bissubstituted-1,1'-N-halo-5,5,5'5'-substituted-2, 2',4,4'-imidazolidinedione; 1,3,8-Triaza-3-substituted-7,7,9, 9-substituted-1,8-N-halo-2,4-dioxospiro[4.5]decane; 3,3'-disubstituted-bis(7,7,9,9-substituted)-1,3,8-Triazaspiro[4.5] decane-1,1',8,8'N-halo-2,4-dione; 8,8'-disubstituted-bis(7,7, 9,9-substituted)-1,3,8-Triazaspiro[4.5]decane-1,1',3,3'N-halo-2,4-dione; Vinyl chloride-co-3-vinyl-N-halo-5,5-disubstituted hydantoin; Vinyl chloride-co-3-vinyl-1,3,8-Triaza-7,7,9,9-substituted-1,8-N-halo-2,4-dioxospiro[4.5] decane and combinations thereof. However, the skilled artisan will recognize that the 4 to 7 membered rings with one or more nitrogen heteroatoms may be substituted with one or more alkyl groups, alkylene groups, alkenyl groups, alkynyl groups, aryl groups, alkoxy groups, alkylcarbonyl groups, alkylcarboxyl groups, amido groups, carboxyl groups, halogens, hydrogens or combinations thereof.

Additionally, the N-halamine biocidal compound may be in communication with or bonded to, either covalently or ionically, one or more halogens. In addition the presence of halogen may be replenished when concentrations are low doe to activity, diffusion, reactivity, redox reactions through the treatment a hypohalogenic solution, e.g., hypochlorite or hypoborite solution.

The N-halamine biocidal compounds may be integrated into a polymer as stabilization agents, polymeric materials, copolymers, additives or the like. The target material may be a polymer in the form of plastics, cellulose, rubbers, fibers, woods, paints, coatings.

The monomeric and polymeric N-halamine compounds of the present invention for antimicrobial and anti-biofilm applications include the eight (8) basic formulas, as shown in FIG. 1. In these formulas, the N—X (e.g., X is a halogen) structures are stable N-halamines. These compounds can provide potent, durable and rechargeable biocidal functions against bacteria, fungus, yeast, virus and spores. The basic formulas illustrated in FIG. 1 may be substituted with one or more functional groups at one or more of the R positions, e.g., $R^1$-$R^{10}$. The skilled artisan will recognize that the R substitution may take many forms, e.g., the R group may independently be an alkyl group, an alkylene group, an alkenyl group, an alkynyl group, an aryl group, an alkoxy group, an alkylcarbonyl group, an alkylcarboxyl group, an amido group, a carboxyl group or a halogen. Further more the R group may be substituted with one or more alkyl groups, alkylene groups, alkenyl groups, alkynyl groups, aryl groups, alkoxy groups, alkylcarbonyl groups, alkylcarboxyl groups, amido groups, carboxyl groups or halogens.

In one example of the synthesis of the N-halamine compounds with the general formula 1 as shown in FIG. 1, 5,5-dimethylhydantion (DMH) was purchased from Acros Organics, 1-bromoethane (BE), 1-bromobutane (BB), 1-bromohexane (BH), 1-bromododecane (BD) and 1-bromooctadecane (BOD) were provided by ALDRICH, 1-bromodocosane (BDCS) by Tokyo Kasei Kogyo Co. LTD. Trichloroisocyanuric acid (99%, TCCA) used as a chlorinating agent was obtained from Acros Organics. All chemicals were used without further purification. The synthesis process is illustrated below.

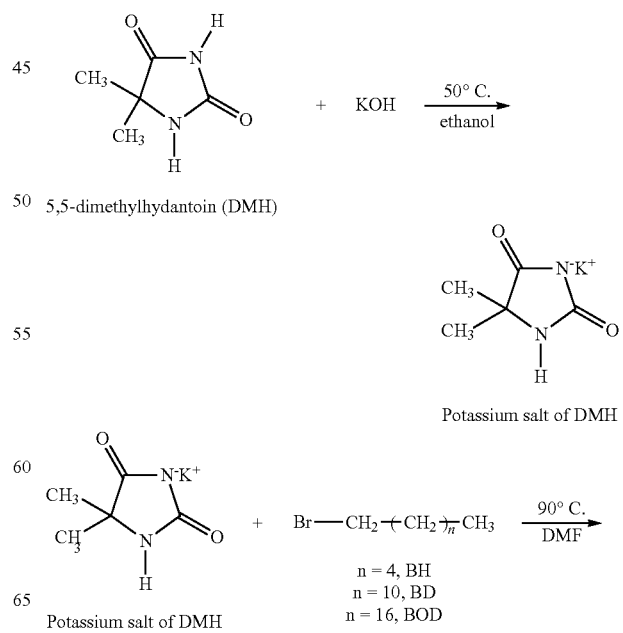

-continued

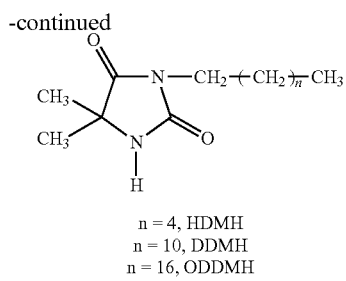

n = 4, HDMH
n = 10, DDMH
n = 16, ODDMH

To about 30 mL of methanol solution containing 0.025 mol (e.g., 3.20 g) of DMH was added to about 0.03 mol (e.g., 1.68 g) of potassium hydroxide. The mixture was heated and kept at about 50° C. for about 30 minutes After evaporation of the methanol and the water produced in the reaction under reduced pressure, the solid potassium salt of DMH was dried in a vacuum oven at about 60° C. for three days to form the anhydrous potassium salt. The dry salt was then mixed with about 100 mL of N,N-dimethylformamide (DMF) at about 95° C. for about 10 minutes under constant stirring, and about 0.025 mol of 1-brominated hydrocarbon was added, and the solution was reacting for about 2 hours.

3-ethyl-5,5-dimethylhydantoin (EDMH). After reaction, the solid in the reaction solution was filtered off and the DMF solvent in the filtrate was removed by distillation under reduced pressure. The residual substance was recrystallized from distilled water. 3.65 grams of EDMH was received as a white powder, yield: 93.5%.

3-butyl-5,5-dimethylhydantoin (BDMH). After reaction, the solid in the reaction solution was filtered off and the DMF solvent in the filtrate was removed by distillation under reduced pressure. The residual substance was isolated with chloroform. After evaporation of chloroform, 3.75 grams of BDMH was obtained as transparent viscous liquid, yield: 81.5%.

3-hexyl-5,5-dimethylhydantoin (HDMH). 3.50 grams of HDMH was obtained as transparent viscous liquid following the same procedure described in BDMH, yield: 66.0%.

3-dodecyl-5,5-dimethylhydantoin (DDMH). 6.23 grams of BD. After reaction, the solid in the reaction solution was filtered off and the filtrate was cooled to 0° C. The precipitate was isolated by filtration and recrystallized from methanol. 7.10 grams of DDMH was obtained as a white powder, yield: 95.9%.

3-octadecyl-5,5-dimethylhydantoin (ODDMH). 8.34 grams of BOD. 8.20 grams of ODDMH was obtained as a white powder following the same procedure described in DDMH, yield: 86.2%.

3-docosanyl-5,5-dimethylhydantoin (DCSDMH). 9.74 grams of BDCS. 10.20 grams of DCSDMH was obtained as a white powder following the same procedure described in DDMH, yield: 93.4%.

General procedure for the synthesis of chlorinated 3-alkyl-5,5-dimethylhydantoin. 3-alkyl-5,5-dimethylhydantoin and trichloroisocyanuric acid (e.g., TCCA, molar ratio 1:3) were dissolved in acetone. The solution was vigorously stirred for 30 minutes at room temperature and then the acetone solvent was evaporated. Hexane was added to the mixtures and the insoluble solid was filtered off. After removal of hexane by evaporation, the chlorinated 3-alkyl-5,5-dimethylhydantoin was obtained.

Chlorination of EDMH (Cl-EDMH). After removal of hexane, 0.4741 grams of Cl-EDMH was obtained as a while powder, yield: 50.0%. Chlorine content determined by titration is 20.11% (theoretical: 18.63%).

Chlorination of BDMH (Cl-BDMH). 0.9378 grams (0.005 mol) of BDMH, 3.50 grams (0.015 mol) of TCCA. After removal of hexane, 0.7890 grams of Cl-BDMH was obtained as a white powder, yield: 72.2%. Chlorine content determined by titration is 18.39% (theoretical: 16.24%).

Chlorination of DMH-BH (Cl-HDMH). 0.9352 grams (0.0044 mol) of HDMH, 3.10 grams (0.0132 mol) of TCCA. After removal of hexane, 0.7112 grams of Cl-HDMH was obtained as transparent viscous liquid, yield: 65.5%. Chlorine content determined by titration is 12.83% (theoretical: 14.39%).

Chlorination of DDMH (Cl-DDMH). 0.8477 grams (0.0029 mol) of DDMH, 2.00 grams (0.01 mol) of TCCA. After removal of hexane, 0.92 grams of Cl-DDMH was obtained as transparent viscous liquid, yield: 97.3%. Chlorine content determined by titration is 10.78% (e.g., theoretical: 10.73%).

Chlorination of ODDMH (Cl-ODDMH). 1.0058 grams (0.0026 mol) of ODDMH, 2.00 grams (0.0078 mol) of TCCA. After removal of hexane, 0.9844 grams of Cl-ODDMH was obtained as a white powder, yield: 91.2%. Chlorine content determined by titration is 7.93% (e.g., theoretical: 8.55%). Chlorination of DCSDMH (Cl-DCSDMH). 0.8698 grams (0.002 mol) of DCSDMH, 1.40 grams (0.006 mol) of TCCA. After removal of hexane, 0.8133 grams of Cl-DCSDMH was obtained as a white powder, yield: 86.3%. Chlorine content determined by titration is 7.68% (e.g., theoretical: 7.54%).

The present invention includes a self-decontaminating biocidal composition having the general formula 2 below.

Formula 2

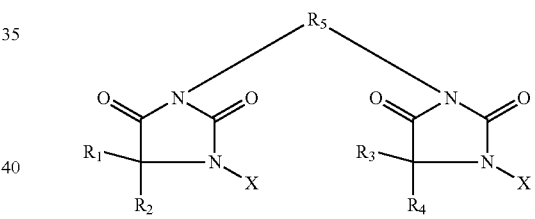

The structure includes two heterocyclic 5-membered rings with each having 2 nitrogen heteroatoms, 2 carbonyl groups and groups $R^1$, $R^2$ and $R^3$, $R^4$, respectively. The two heterocyclic 5-membered rings are connected by group $R^5$ attached to the nitrogen heteroatoms of each of the 5-membered rings. Each of the heterocyclic 5-membered rings includes either hydrogen or a halogen as group X connected to the heteroatom of the 5-membered ring. $R^1$, $R^2$, $R^3$, $R^4$ and $R^5$ may be individually be an alkyl, an alkylene, an alkenyl, an alkynyl, an aryl, an alkoxy, an alkylcarbonyl, an alkylcarboxyl, an amido, an amine, a halogen, a hydrogen, a carboxyl, an aromatic ring or combinations thereof. In addition, each of the $R^1$, $R^2$, $R^3$, $R^4$ and $R^5$ groups may themselves be individually modified and/or substituted with one or more an alkyl, an alkylene, an alkenyl, an alkynyl, an aryl, an alkoxy, an alkylcarbonyl, an alkylcarboxyl, an amido, a carboxyl or an aromatic ring groups.

Preparation of N-halamine-containing materials. In one example, a predetermined amount of Cl-ODDMH (e.g., 1%, 2% and 4% to PU) was added into 5% polyurethane (Noveon) solutions in THF under constant stirring to from a clear solution. The solution was cast onto Teflon sheets in a fume hood at room temperature for 2 days to produce thin films (e.g., 170±10 μm of thickness). The films were further dried under vacuum at 50° C. for 3 days. Cl-ODDMH-containing PU sheets (e.g., 4×4 cm) or discs (e.g., 0.5 cm of diameter) were cut sterilely from the films. Pure PU sheets or discs were prepared under the same conditions as controls.

In another example, a predetermined amount of Cl-ODDMH was added into about 5 percent PP solutions in hot o-xylene under constant stirring. After evaporation of the solvent, polymer films (e.g., thickness: about 70±5 µm) were obtained by hot pressing at about 170° C. for about 15 seconds. Chlorine contents of the resultant samples were determined by iodimetric titration. ODDMH-containing PP films were prepared using the same method.

In another example, a predetermined amount of Cl-BDMH was added into 5% cellulose acetate acetone solution. The solution was coated onto wood, and cured at 60° C. for 10 minutes to form a coating.

In another example, a predetermined amount of Cl-DC-SDMH was added into a commercial paint. The paint was painted onto glass slides to form paintings. Yet in another example, a predetermined amount of HDMH was extruded through an extruder with polyethylene, the extruded polymers were pressed into films, and films were exposed to chlorine bleach.

Anti-biofilm functions. The samples were immersed individually in sealed tubes containing 5 mL of *S. epidermidis* broth suspension ($10^6$-$10^7$ CFU/mL of bacteria) in a shaking water bath at 37° C. and 30 RPM. After 3 days of growth at 37° C. and 30 RPM (which showed substantial biofilm formation on untreated samples), the samples were taken out of the bacteria-containing tubes, washed individually with PBS (3×10 mL) to remove loosely-attached bacteria, sonicated for 20 minutes, and then vortexed for 60 seconds. The solution was serially diluted, and 100 µL of each dilution was plated onto agar plates. The same procedure was applied to the untreated samples as controls. Bacterial colonies were counted after incubation at 37° C. for between about 24 and 48 hours. SEM studies were used to confirm the biofilm controlling function. PU discs with or without the presence of Cl-ODDMH were immersed in 5 mL $10^6$-$10^7$ CFU/mL of *S. epidermidis* broth suspensions in a water bath at 37° C. and 30 RPM. After 3 days of incubation, the discs were rinsed with 0.1 M sodium cacodylate buffer (SCB) at pH 7.4 (e.g., 3×10 mL) to remove loosely-attached cells, and then fixed with 3% glutaraldehyde in SCB for 24 hours. After being gently washed with SCB, the samples were dehydrated through an alcohol gradient,[16] dried in a critical point drier, mounted onto sample holders, sputter coated with gold-palladium, and observed under a SEM (e.g., Philips 515 SEM) to check for the presence of biofilms.

Durability is an important feature of the antimicrobial functions of the samples. After storage at about 25° C. and about 80% RH for 3 months, the biofilm-controlling functions were unchanged. Evaluation of the rechargeability of the samples were preformed by first treated with about 1.0 weight percent sodium thiosulfate solutions at room temperature for about 120 minutes to partially quench the chlorine, and then re-chlorinated with about 0.6 weight percent sodium hypochlorite solutions. After about 20 cycles of the re-chlorinating treatments, the chlorine contents and antimicrobial activities of the samples were essentially unchanged, indicating that the antimicrobial functions were fully rechargeable.

The N-halamine-containing material demonstrated anti-biofilm functions. As an example, for polyurethane samples containing 4% Cl-ODDMH, after three days of immersion in *S. epidermidis*, less than 50 CFU/cm$^2$ of bacteria can be recovered from the samples, while for pure polyurethane samples, under the same conditions, the recovered bacteria were higher than $10^5$ CFU/cm$^2$. After three days, substantial biofilms were found on pure polyurethane, but no biofilm on the N-halamine-containing samples were observed, only limited scattered bacteria could be detected in SEM studies.

Preparation of CADMH-containing polymeric materials. PS and HDPE were used as the model polymers to preliminarily evaluate the antimicrobial activities of CADMH as additives. In the preparation of CADMH-containing PS films, a certain amount of CADMH was dissolved in 5% PS solutions in THF. The solution was poured onto glass slides. The glass slides were put in a fume hood for 2 days at room temperature to evaporate most of the solvent, and then further dried in a vacuum oven at 30° C. for 3 days to obtain polymer films (100±10 µm of thickness). To prepare CADMH-containing HDPE films, a predetermined amount of CADMH was added into 5% HDPE solutions in hot o-xylene under constant stirring. After evaporation of the solvent, polymer films having a thickness of about 70±5 µm were obtained by hot pressing at 140° C. for 15 seconds. The chlorine contents of the CADMH-containing PS and HDPE films were determined by iodimetric titration, as described above. Pure PS or HDPE films without the presence of CADMH were prepared using the same procedures as controls.

In other examples to evaluate antimicrobial activities of CADMH, *Escherichia coli* (e.g., *E. coli*, ATCC® 15597™, gram-negative) and *Staphylococcus aureus* subsp. *aureus* (e.g., *S. aureus*, ATCC® 6538™, gram-positive) were used as model microorganisms to challenge the antimicrobial functions of the samples. In the microbial studies, the bacteria were grown in broth solutions (e.g., LB broth for *E. coli*; Tryptic Soy broth for *S. aureus*) overnight at 37° C. Cells were harvested in a centrifuge, washed twice with phosphate buffered saline (e.g., PBS, OmniPur®, NaCl, 8.0 g/L; KCl, 0.20 g/L; $Na_2HPO_4$, 1.42 g/L; $KH_2PO_4$, 1.36 g/L; pH 7.4), re-suspended in PBS, and then diluted to concentrations of $10^{8-9}$ CFU/mL. A known amount of CADMH (particle size: 60-80 mesh) was dispersed in 10 mL of sterilized distilled water. The mixture was vortexed and then sonicated for 10 minutes. Then, 100 µL of the bacteria suspension were added into the CADMH-containing suspension and the resultant mixture was vortexed for 60 seconds. After a certain period of contact time under constant shaking, the mixture was poured into 90 mL of 0.03 wt % sterilized sodium thiosulfate aqueous solution to quench the active chlorine and stop the antimicrobial test. Our previous studies have shown that such a treatment does not affect the growth of the bacteria. The resulting solutions were vortexed for 2 minutes and then serially diluted, and each dilution was placed onto LB agar (for *E. coli*) or Tryptic soy agar (for *S. aureus*). The same procedure was also applied to the correspondent unchlorinated samples as controls. Bacterial colonies on the plates were counted after incubation at 37° C. for 24 hours.

Antimicrobial activity of CADMH-containing polymers. In the antimicrobial tests of CADMH-containing PS or HDPE films, 10 µL of *E. coli* suspensions (e.g., $10^8$-$10^9$ CFU/mL) were placed onto the surface of a film (e.g., 4×4 cm). The film was then covered with another identical film. A 100 grams weight was added onto the whole "sandwich" to ensure sufficient contact. At different contact time, the "sandwich" was transferred into 10 mL of 0.03 wt % sodium thiosulfate aqueous solution to quench the active chlorine of the samples. The mixture was sonicated for 20 minutes and vortexed for 60 seconds to remove the adherent bacteria into the solution. The resultant solution was serially diluted, and each dilution was placed onto LB agar plates. The same procedure was also applied to the pure PS or HDPE films as controls. Bacterial colonies were counted after 24 hours of incubation at 37° C.

Figure 2:
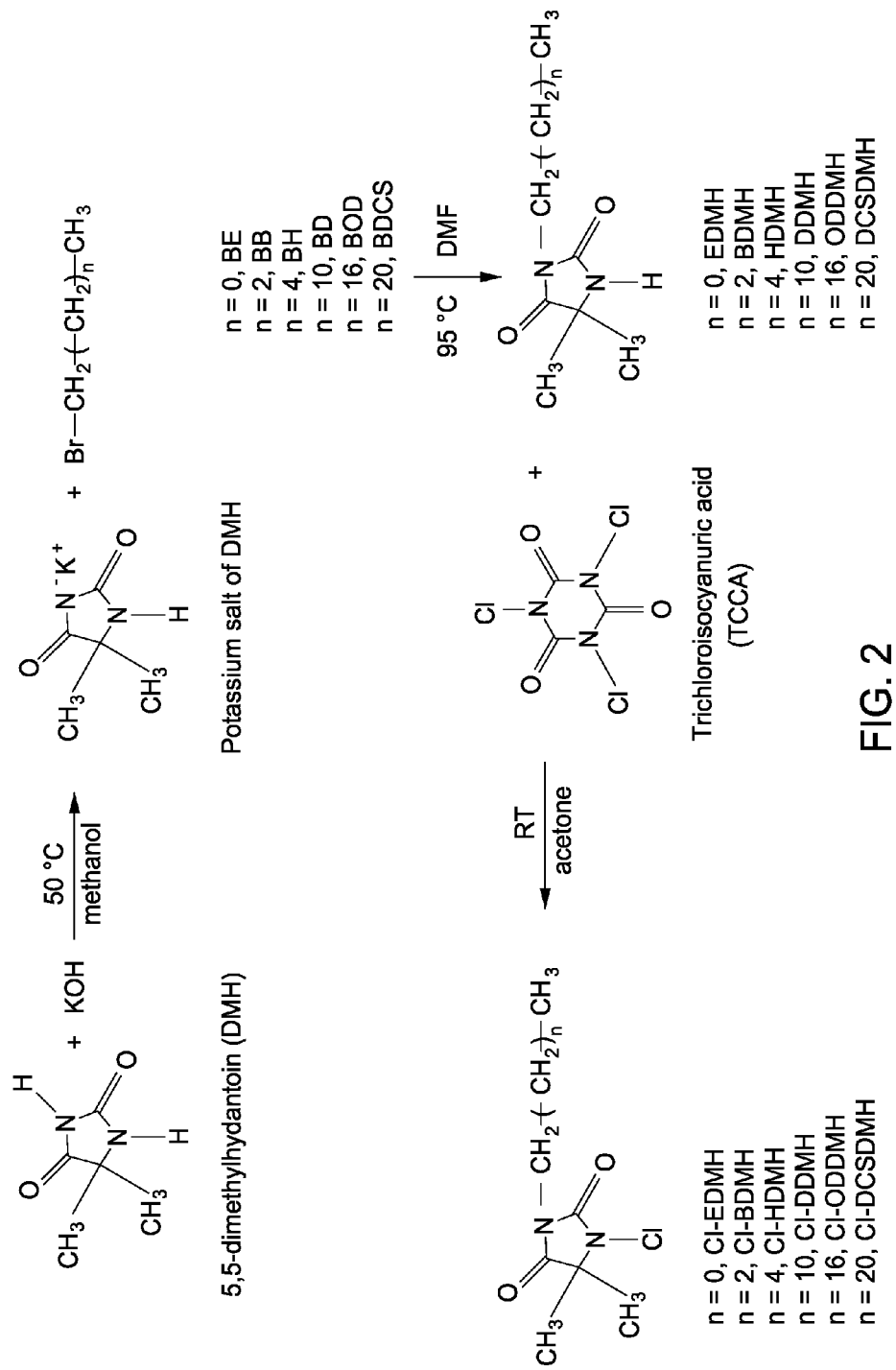
FIG. 2 is a scheme illustrating one method of synthesis of 3-alkyl-5,5-dimethylhydantoins.

To illustrate the synthesis and characterization of the samples, FIG. 2 is a scheme illustrating one method of synthesis of 3-alkyl-5,5-dimethylhydantoins by the nucleophilic reaction of alkyl bromide with the potassium salt of DMH, and CADMH was prepared by the chlorine exchange reaction of TCCA with the 3-alkyl-5,5-dimethylhydantoins. All the reactions preceded smoothly with good yields.

Figure 3:
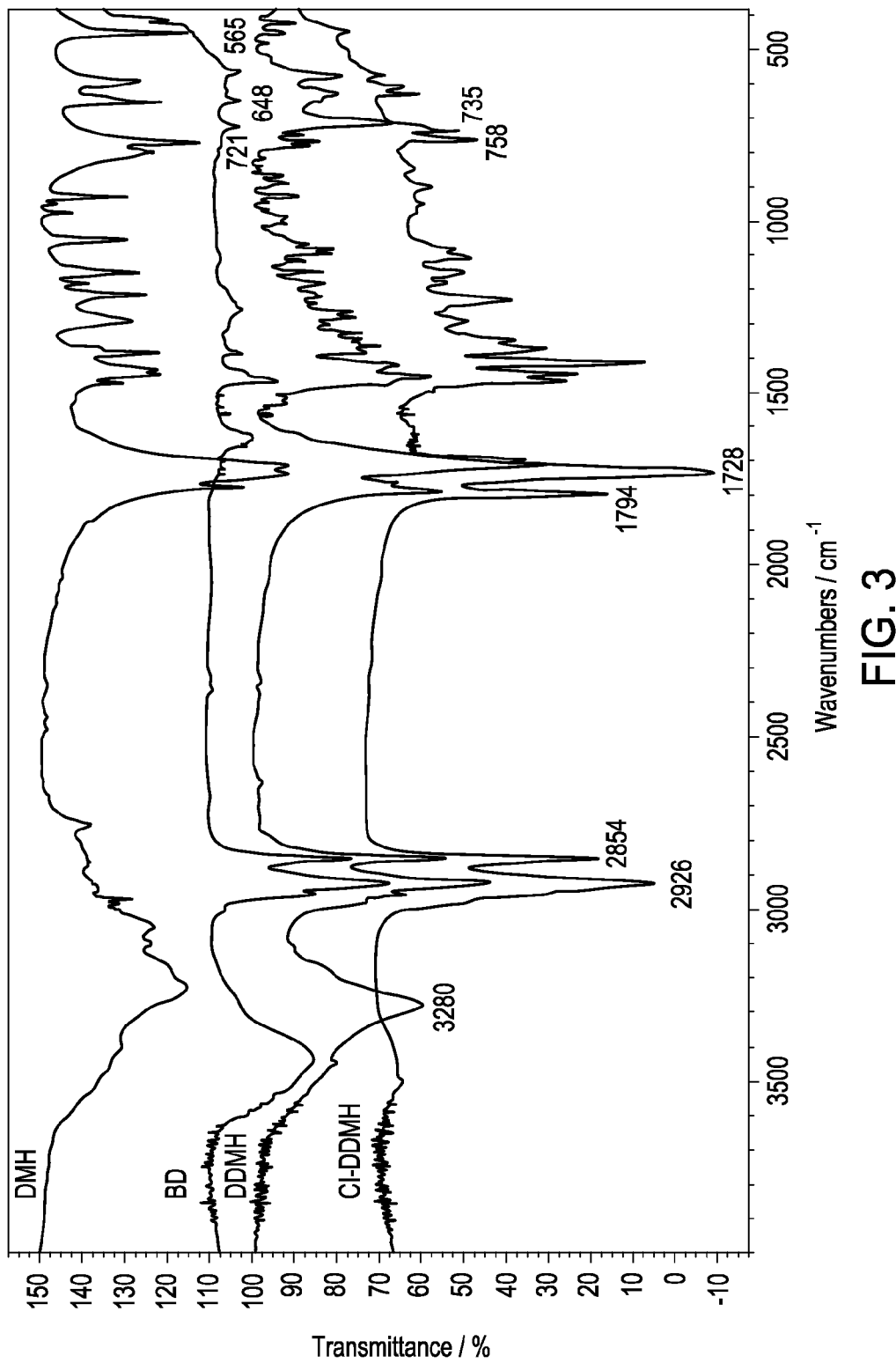
FIG. 3 is an IR spectra of DMH, BD, DDMH and Cl-DDMH.

FT-IR analysis was used to characterize the reactions. As an example, FIG. 3 is an IR spectra of DMH, BD, DDMH and Cl-DDMH. In the spectrum of DMH, the broad peak centered around 3280 $cm^{-1}$ is attributable to N—H stretching vibrations, and the 1770, 1732 and 1713 $cm^{-1}$ bands are caused by the C=O stretching vibrations of the imide and amide groups. The C—H stretching vibrations of BD are presented in the region of 2854 $cm^{-1}$-2956 $cm^{-1}$. In the spectrum of DDMH, the C—H peaks of the alkyl chain can be clearly observed. In addition, the carbonyl bands of the imide and amide groups shift to 1782 $cm^{-1}$ and 1707 $cm^{-1}$, respectively. Upon treatment with TCCA, the N—H bond in DDMH is transformed into N—Cl bond. Consequently, in the spectrum of Cl-DDMH, the N—H stretching vibration around 3280 $cm^{-1}$ disappears, and two new bands at 758 and 735 $cm^{-1}$ can be detected, which are assigned to the N—Cl groups. Moreover, the transformation of N—H bonds to N—Cl groups is associated with the breakage of N—H— O=C hydrogen bonding in DDMH, and this results in the shifts of the C=O bands from 1782 and 1707 $cm^{-1}$ in DDMH to 1794 and 1728 $cm^{-1}$ in Cl-DDMH, respectively.

Figure 4:
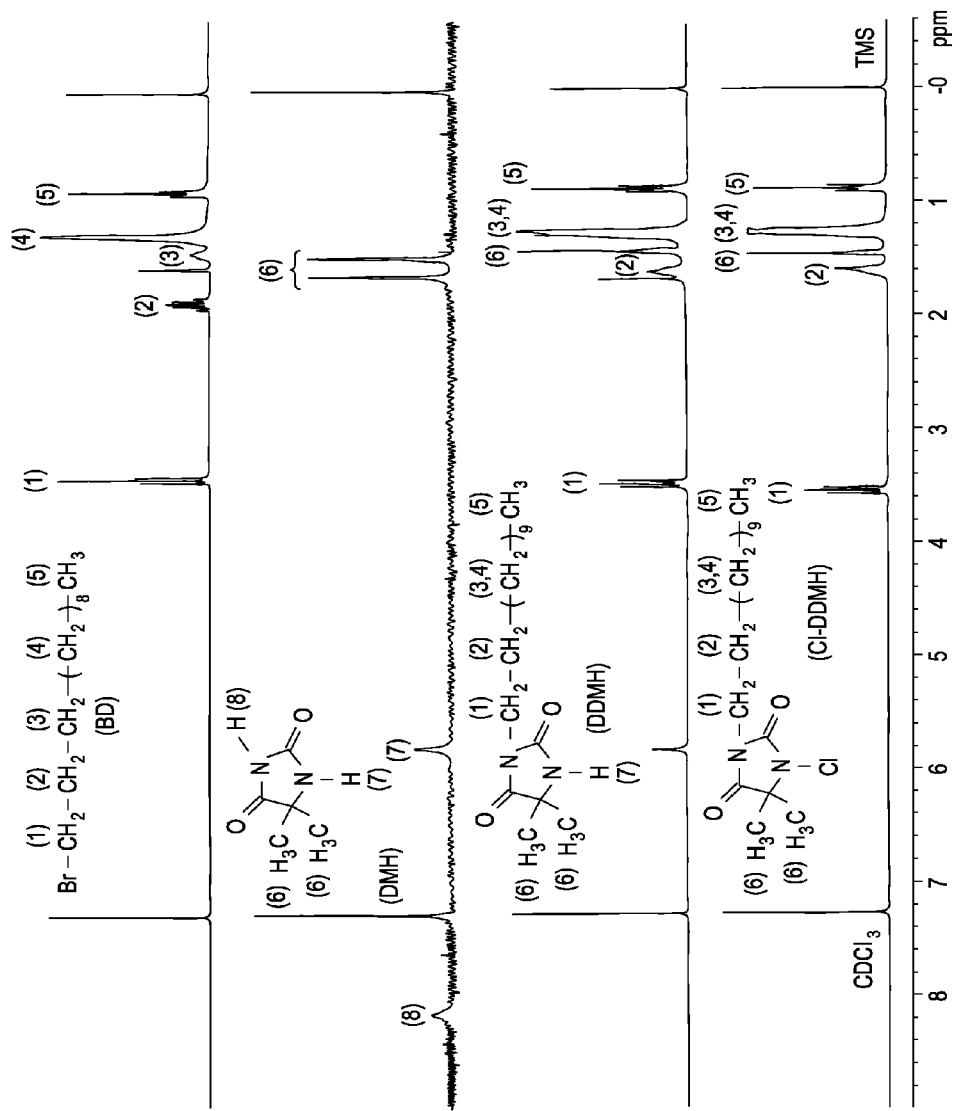
FIG. 4 shows the proton NMR spectra of BD, DMH, DDMH and Cl-DDMH.

The chemical structures of the samples were also characterized with $^1$H NMR analysis. As a typical example, FIG. 4 shows the proton NMR spectra of BD, DMH, DDMH and Cl-DDMH. The assignments of the signals in BD are: δ=3.44 (t, $H^1$), 1.80 (m, $H^2$), 1.46 (m, $H^3$), 1.30 (m, $H^4$) and 0.92 ppm (t, $H^5$). In the spectrum of DMH, the methyl protons show signals at 1.64 and 1.47 ppm, the imide proton shows a resonance peak at 8.14 ppm, and the amide proton displays a single peak at 5.79 ppm. After the substitution reaction of DMH with BD, while the alkyl proton signals of BD and the methyl and amide proton resonances of DMH can be clearly observed in the spectrum of DDMH, the imide proton signal (8.14 ppm in DMH) disappears. After chlorination, the amide proton signal can no longer be detected in the spectrum of Cl-DDMH, indicating that the N—H bond in DDMH is transformed into N—Cl group.

Figure 5:
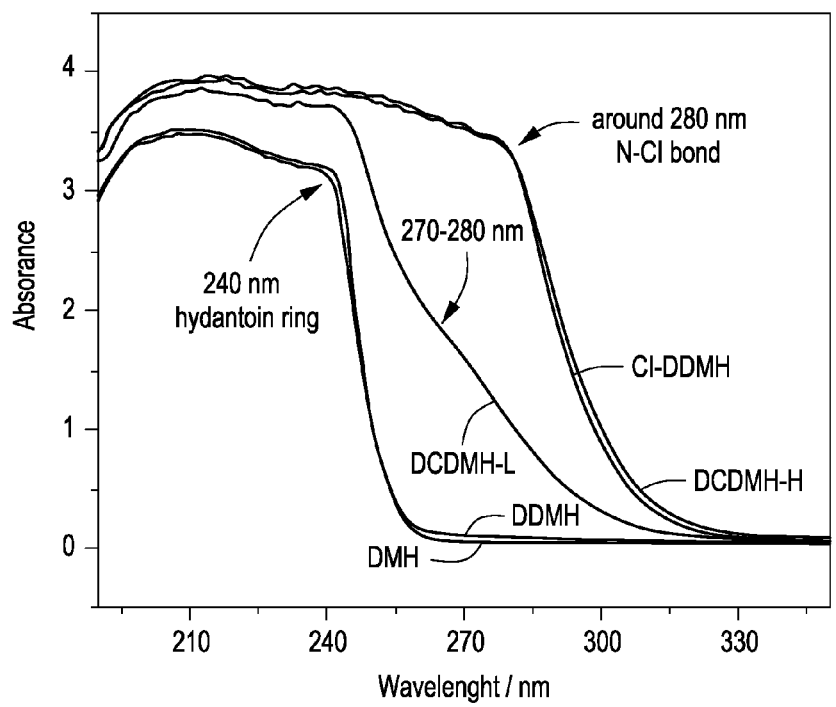
FIG. 5 is a UV spectrum of the N—H→N—Cl transformation.

The N—H→N—Cl transformation was further confirmed by UV analysis; typical examples are presented in the UV spectrum of FIG. 5. In the UV spectra of DMH and DDMH (0.05 mol/L in methanol), the UV adsorption centered at 240 nm are caused by the hydantoin ring structures. After chlorination, DMH is transformed into 1,3-dichloro-5,5-dimethylhydantoin (DCDMH), and DDMH is transformed into Cl-DDMH. At a concentration of 0.05 mol/L, a broad N-halamine peak around 280 is clearly observed in the UV spectra of DCDMH-H and Cl-DDMH, which can be caused by the disruption of the N—Cl bond and/or the transition from a bonding to an antibonding orbital. The presence of the 280 nm absorption is further confirmed by the UV spectrum of diluted DCDMH methanol solution (DCDMH-L, 0.01 mol/L). In this spectrum, in addition to the strong hydantoin ring adsorption at 240 nm, a weak shoulder in the range of 270-280 nm can be detected. The UV spectrum of diluted Cl-DDMH was also examined. Unfortunately, because of the relatively low chlorine content of Cl-DDMH (10.78% vs. 36.04% in DCDMH) and the interference of the strong adsorption of the ring structure, the N—Cl adsorption in diluted Cl-DDMH was too weak to be detectable. Similar phenomena are also observed in the UV study of other CADMH.

Figure 6:
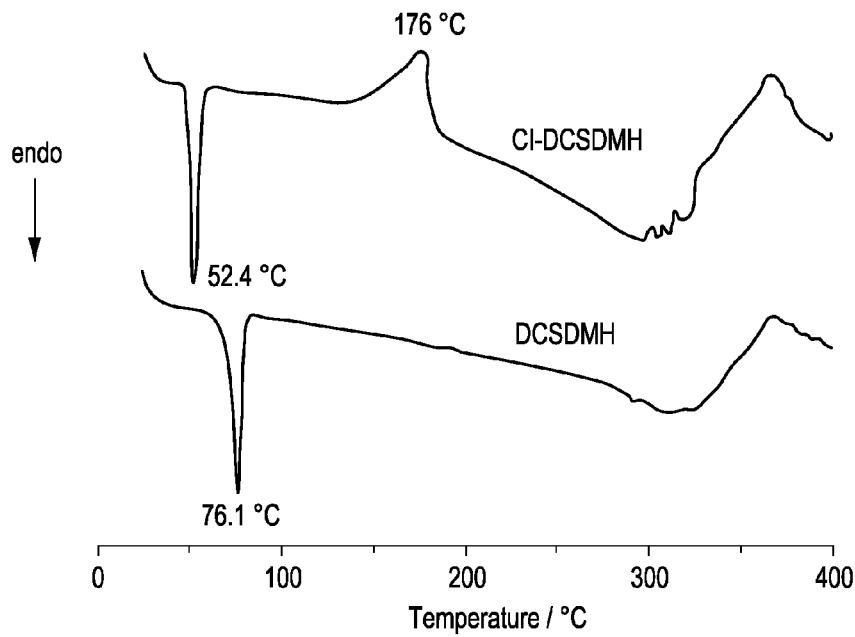
FIG. 6 illustrates DSC curves showing DCSDMH and Cl-DCSDMH.

Thermal properties of the samples were examined with DSC, and the representative DSC curves are shown in FIG. 6 using DCSDMH and Cl-DCSDMH as examples. DCSDMH shows a sharp melting peak at 76.1° C. After chlorination, the N—H bond in DCSDMH is transformed into N—Cl group, and because of the lack of hydrogen bonding, the melting point of Cl-DCSDMH decreases to 52.4° C. Moreover, an intensive exothermic peak at 176.0° C. is observed in the DSC curve of Cl-DCSDMH, which can be caused by the decomposition of the N—Cl bond.

Figure 7A:
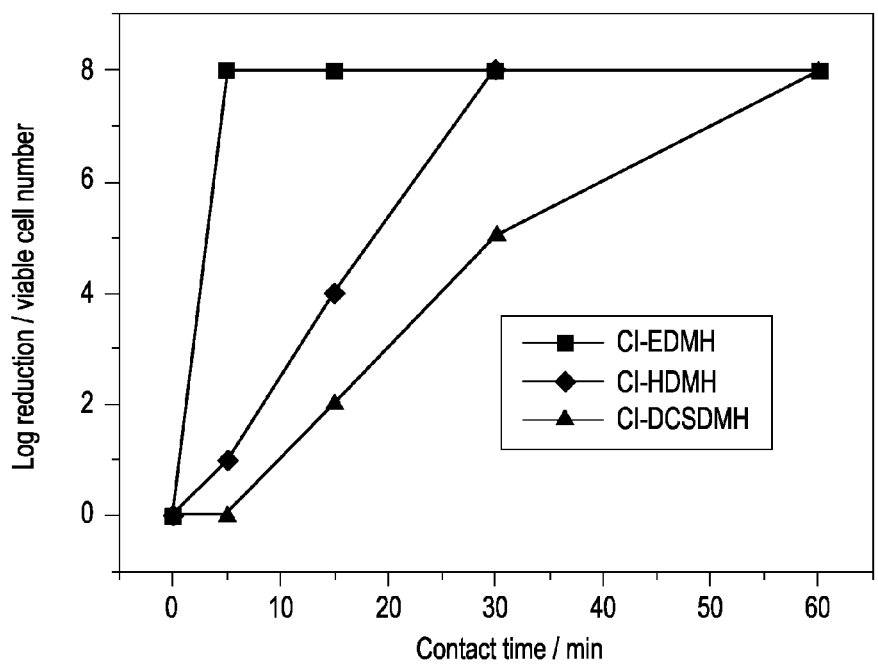
FIGS. 7A and 7B are graphs of the cells killed using 500 ppm of active chlorine.
Figure 7B:
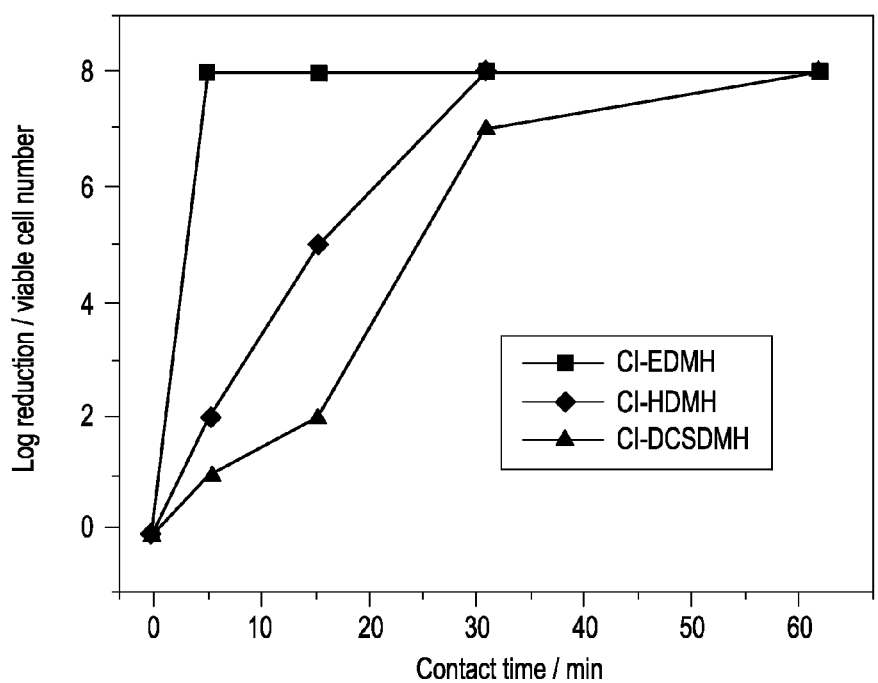
Figure 8A:
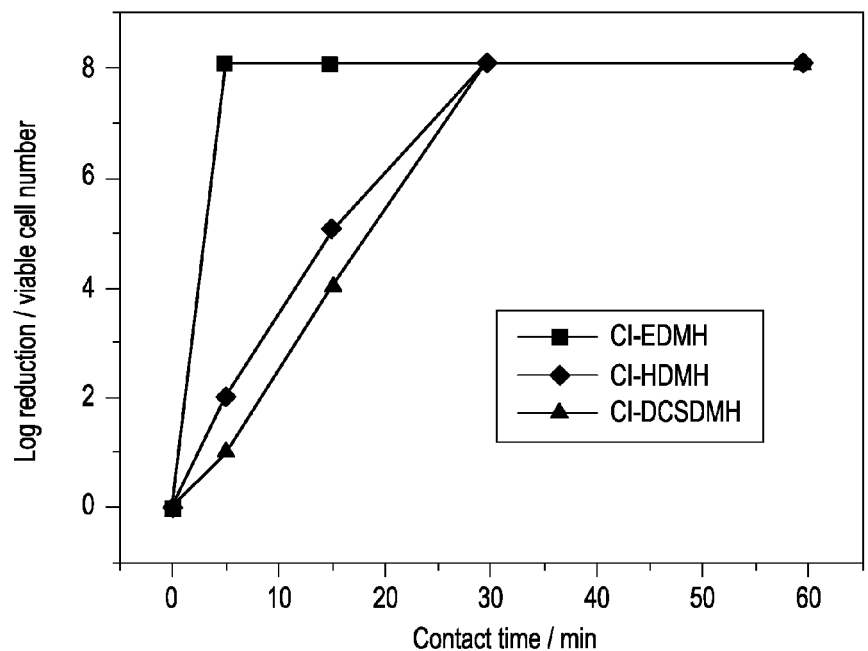
FIGS. 8A and 8B are graphs of the cells killed using 1000 ppm of active chlorine.
Figure 8B:
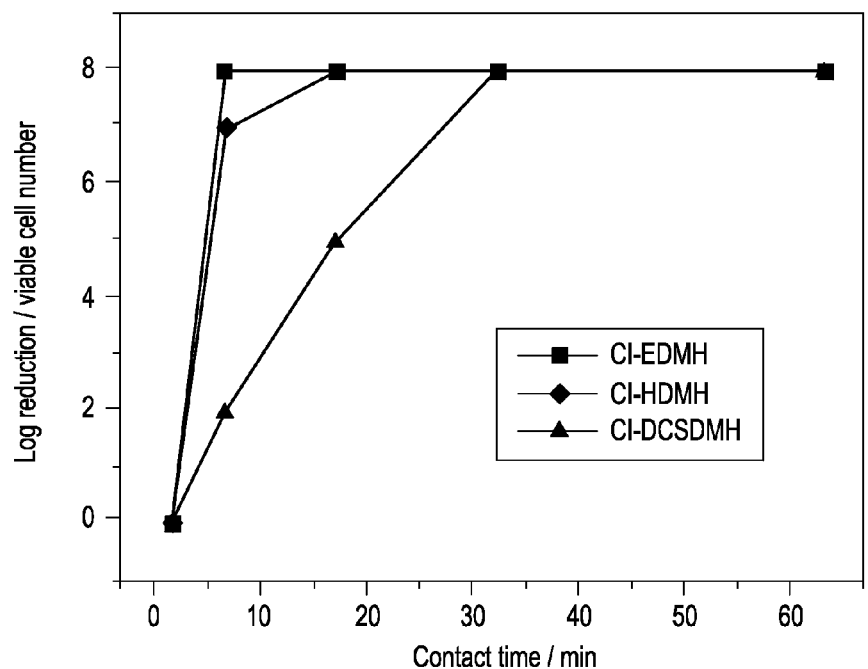
Figure 16:
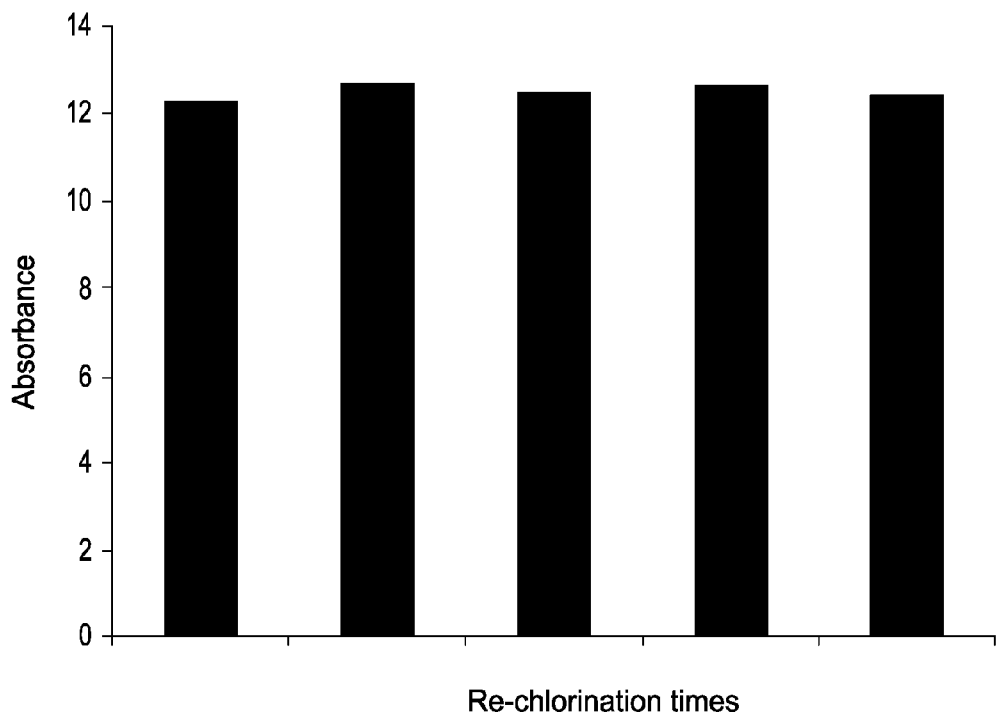
FIG. 16 is a graph of the chlorine content of Cl-BTMP after different cycles of re-chlorination treatments.

Antimicrobial functions. The antimicrobial activities of CADMH were challenged with gram-negative (E. coli) and gram-positive (S. aureus) bacteria. All the samples provided potent antimicrobial functions against both species. As a general observation, shorter alkyl chain length leads to faster antimicrobial actions. For instance, as shown in the graph of FIG. 7, at 500 ppm of active chlorine content, Cl-EDMH provides a total kill of $10^8$-$10^9$ CFU/mL of E. coli and S. aureus in less than 5 minutes. However, it takes Cl-HDMH 30 minutes and Cl-DCSDMH 60 minutes to achieve the same antimicrobial efficacy. Antimicrobial activities of Cl-EDMH, Cl-HDMH and Cl-DCSDMH against FIG. 7(a) E. coli (gram-negative bacteria) and FIG. 7(b) S. aureus (gram-positive bacteria). The active chlorine content in the test suspensions was 500 ppm. When the active chlorine content is increased to 1000 ppm as seen in the graph of FIG. 16, the antimicrobial activities of Cl-HDMH and Cl-DCSDMH are significantly improved with about 20-30 minutes for total kill, but their bactericidal actions are still slower than that of Cl-EDMH with less than 5 minutes for total kill. Antimicrobial activities of Cl-EDMH, Cl-HDMH and Cl-DCSDMH against FIG. 8(a) E. coli (gram-negative bacteria) and FIG. 8(b) S. aureus (gram-positive bacteria).

It has been reported that the bactericidal action of N-halamines is a manifestation of a chemical reaction involving the direct transfer of positive chlorines from the N-halamines to the appropriate receptors in the cells. This chemical reaction can effectively destroy or inhibit enzymatic or metabolic cell processes, resulting in the expiration of the organisms. With the increase of alkyl chain length, the solubility of the CADMH decreases. As a matter of fact, while Cl-EDMH is soluble in water (ca. 3 g/L at 23° C.), both Cl-HDMH and Cl-DCSDMH are insoluble. The water solubility of Cl-EDMH ensures full contact of the bacteria with Cl-EDMH molecules in the antimicrobial tests, resulting in the most potent antimicrobial activity with a total kill in less than 5 minutes. In the cases of Cl-HDMH and Cl-DCSDMH, however, the bacteria could only contact with the surfaces of the Cl-HDMH and Cl-DCSDMH particles (60-80 mesh) during the microbial tests. Thus, longer contact time is needed for a total kill of the microorganisms.

It is interesting to note that the CADMH provided faster antimicrobial action against gram-positive bacteria than gram-negative bacteria. For example, at 1000 ppm of active chlorine content, after 5 minutes of contact, Cl-HDMH provides 2 log reduction (99% of kill) of E. coli, but it offers 7 log reduction (99.99999% of kill) of S. aureus as seen in FIG. 8. When the contact time is extended to 15 minutes, Cl-HDMH provides 5 log reduction of E. coli (99.999% of kill), but it inactivates all the S. aureus tested (8 log reduction). This difference can be attributed to the different structures of the bacteria. A major structural difference between gram-negative bacteria and gram-positive bacteria is that the cell wall of the former is overlaid with an outer membrane comprising lipopolysaccharide. This lipopolysaccharide layer offers a supplementary barrier limiting or preventing the penetration of antimicrobial agents into the cell. Therefore, *E. coli* (gram-negative) are inactivated in a longer contact period than *S. aureus* (gram-positive).

The CADMH showed excellent storage stability. After storage for about 4 months under ambient conditions (e.g., 23±2° C., 70±5% RH), all the samples retained more than 96% of their original chlorine contents. The antimicrobial functions were tested monthly during the storage period, and after 4 months of storage, the minimum contact time of the samples for a total kill of $10^8$-$10^9$ CFU/mL of *E. coli* or *S. aureus* was unchanged.

The efficacy of CADMH as antimicrobial additives in polymeric materials was preliminarily evaluated. PS and HDPE were used as model polymers. CADMH samples were added into PS through solvent casting, and they were incorporated into HDPE though hot pressing. Iodimetric titration showed that these two approaches did not affect the chlorine contents of the CADMH samples, suggesting the suitability of CADH as potential polymer additives. While neither the original PS nor the HDPE had any antimicrobial effects, the CADMH-containing materials provided potent antimicrobial functions. For instance, when as low as 1% of Cl-DCSDMH was added into PS or HDPE films, the resultant films provided a total kill of $10^8$-$10^9$ CFU/mL of *E. coli* (the more resistant species than *S. aureus*) after 4 hours of contact. After storage for 4 months at 23±2° C. and 70±5% RH, no changes could be observed in the active chlorine contents and the antimicrobial activities of the Cl-DC-SDMH-containing PS and HDPE films. Although more studies are needed to further evaluate their performances, these findings point to the great potentials of the CADMH as effective antimicrobial additives for polymeric materials.

The present invention includes a self-decontaminating biocidal composition having the general formula 3 below.

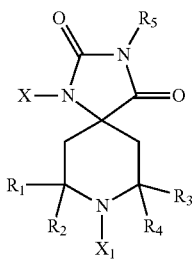

Formula 3

The bicyclic ring structure (e.g., Spiro rings structure sharing a common atom) includes a heterocyclic 5-membered ring and a heterocyclic 6-membered ring. The heterocyclic 5-membered ring has 2 nitrogen heteroatoms, 2 carbonyl groups and a $R^5$ group connected to one of the nitrogen heteroatoms. The heterocyclic 6-membered ring has a nitrogen heteroatom and groups $R^1$, $R^2$, $R^3$ and $R^4$. Each of the ring structures includes a hydrogen or a halogen at positions X and $X_1$. $R^1$, $R^2$, $R^3$, $R^4$ and $R^5$ may be individually be an alkyl, an alkylene, an alkenyl, an alkynyl, an aryl, an alkoxy, an alkylcarbonyl, an alkylcarboxyl, an amido, an amine, a halogen, a carboxyl, an aromatic ring or combinations thereof. In addition, each of the $R^1$, $R^2$, $R^3$, $R^4$ and $R^5$ groups may themselves individually be modified and/or substituted with one or more an alkyl, an alkylene, an alkenyl, an alkynyl, an aryl, an alkoxy, an alkylcarbonyl, an alkylcarboxyl, an amido, a carboxyl or an aromatic ring groups.

The present invention includes a self-decontaminating biocidal composition having the general formula 4 below.

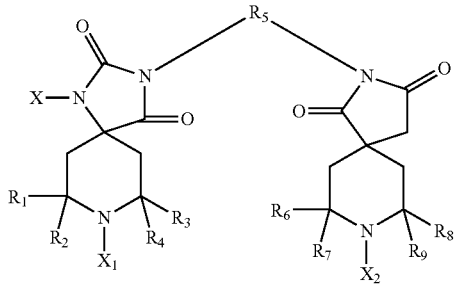

Formula 4

The structure includes 2 bicyclic ring structures connected by a group $R^5$ attached to the heteroatom of each of the bicyclic rings. Each of the bicyclic ring structures has a heterocyclic 5-membered ring and a heterocyclic 6-membered ring (e.g., spiro rings structure sharing a common atom). The heterocyclic 5-membered ring has 2 nitrogen heteroatoms and 2 carbonyl groups. The heterocyclic 5-membered ring has a group X attached to one of the heteroatoms that may be a hydrogen or a halogen. Similarly, the heterocyclic 6-membered ring has an $X^1$ group that may be Hydrogen or a halogen attached to the heteroatom. The 2 bicyclic ring structures include groups $R^1$, $R^2$, $R^3$, $R^4$, $R^5$, $R^6$, $R^7$, $R^8$ and $R^9$ respectively. $R^1$, $R^2$, $R^3$, $R^4$, $R^5$, $R^6$, $R^7$, $R^8$ and $R^9$ may be individually be an alkyl, an alkylene, an alkenyl, an alkynyl, an aryl, an alkoxy, an alkylcarbonyl, an alkylcarboxyl, an amido, an amine, a halogen, a hydrogen, a carboxyl, an aromatic ring or combinations thereof. In addition, each of the $R^1$, $R^2$, $R^3$, $R^4$, $R^6$, $R^7$, $R^8$ and $R^9$ groups may themselves individually be modified and/or substituted with one or more an alkyl, an alkylene, an alkenyl, an alkynyl, an aryl, an alkoxy, an alkylcarbonyl, an alkylcarboxyl, an amido, an amine, a halogen, a hydrogen, a carboxyl or an aromatic ring groups.

Additionally, the present invention includes a self-decontaminating biocidal composition having the general formula 5 below.

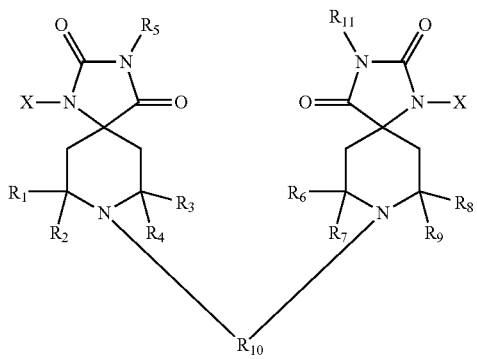

Formula 5

The structure includes 2 bicyclic ring structures connected at the heteroatoms through group $R^{10}$. Each of the bicyclic ring structures has a heterocyclic 5-membered ring and a heterocyclic 6-membered ring (e.g., spiro rings structure sharing a common atom). The heterocyclic 5-membered ring has 2 nitrogen heteroatoms, 2 carbonyl groups and groups $R^5$ and $R^{11}$ respectively. The heterocyclic 5-membered ring also has group X that may be a hydrogen or a halogen attached to one of the heteroatoms. The heterocyclic 6-membered ring has a nitrogen heteroatom and groups $R^1$, $R^2$, $R^3$, $R^4$ and $R^6$, $R^7$, $R^8$, $R^9$ respectively. Groups $R^1$, $R^2$, $R^3$, $R^4$, $R^5$, $R^6$, $R^7$, $R^8$, $R^9$, $R^9$ and $R^{11}$ may be individually be an alkyl, an alkylene, an alkenyl, an alkynyl, an aryl, an alkoxy, an alkylcarbonyl, an alkylcarboxyl, an amido, a carboxyl, an aromatic ring or combinations thereof. In addition, each of the $R^1$, $R^2$, $R^3$, $R^4$, $R^5$, $R^6$, $R^7$, $R^8$, $R^9$, $R^9$ and $R^{11}$ groups may themselves individually be modified and/or substituted with one or more an alkyl, an alkylene, an alkenyl, an alkynyl, an aryl, an alkoxy, an alkylcarbonyl, an alkylcarboxyl, an amido, an amine, a halogen, a hydrogen, a carboxyl or an aromatic ring groups.

In other examples to show the synthesis of N-halamine-based chemical with general formula 3 as shown in FIG. 1, 1-bromohexane (BH), 1-bromododecane (BD), 1-bromooctadecane (BOD) and 7,7,9,9-tetramethyl-1,3,8-triazaspiro[4.5]decane-2,4-dione (TMTDD) are available from ALDRICH. Before use, the BH, BD and BOD were distilled at 80° C. and reduced pressure to remove impurities; TMTDD powder were dissolved in dilute sodium hydroxide solution and re-precipitated by the addition of hydrochloric acid, after filtering, the received white samples were thoroughly washed with distilled water.

To a one-neck-round-bottom flask was added a mixture of 30 mL of absolute ethanol, 5.63 grams (0.025 mol) of TMTDD, and 1.68 grams (0.03 mol) of potassium hydroxide. The mixture was heated to form a clear solution. Then the solid potassium salt of the TMTDD was isolated by evaporation of the ethanol solvent and the water produced in the reaction under reduced pressure. This slat was dried under vacuum at 60° C. for three days to form the anhydrous potassium salt. The dry salt was then placed back in the flask fit with condenser where it was mixed with 150 mL of anhydrous N,N-dimethylformamide (DMF), and 0.025 mol of 1-brominated hydrocarbon. The mixture was then heated at 95° C., keeping constant stirring, for 4 hours. After completion of the reaction, the reaction mixture was cooled, and the solid was removed by filtration. The DMF solvent was removed by distillation and the residual substance was recrystallized from absolute ethanol.

7,7,9,9-tetramethyl-3-hexyl-1,3,8-triazaspiro[4,5]decane-2,4-dione (TMTDD-BH) 4.13 grams of BH. After recrystallization, 6.82 grams of 7,7,9,9-tetramethyl-3-hexyl-1,3,8-triazaspiro[4.5]decane-2,4-dione (TMTDD-H, white crystals) was obtained, indicating 88.2% yield. 7,7,9,9-tetramethyl-3-octadecyl-1,3,8-triazaspiro[4,5]decane-2,4-dione (TMTDD-BD) 6.23 grams of BD. After recrystallization, 8.24 grams of 7,7,9,9-tetramethyl-3-dodecyl-1,3,8-triazaspiro[4.5]decane-2,4-dione (TMTDD-D, white crystals) was obtained, indicating 83.7% yield. 7,7,9,9-tetramethyl-3-stearyl-1,3,8-triazaspiro[4,5]decane-2,4-dione (TMTDD-BOD) 8.34 grams of BOD. After recrystallization, 11.09 grams of 7,7,9,9-tetramethyl-3-octadecyl-1,3,8-triazaspiro[4.5]decane-2,4-dione (TMTDD-OD, white crystals) was obtained, indicating 92.9% yield.

The present invention includes a self-decontaminating monomeric or polymeric biocidal composition having the general formula 6 below.

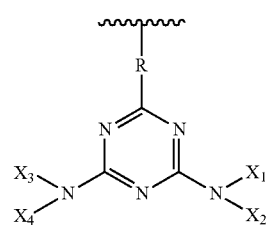

Formula 6

The structure includes a heterocyclic 6-membered ring having 3 nitrogen heteroatoms and 2 amine groups having $X^1$, $X^2$ and $X^3$, $X^4$, respectively. The heterocyclic 6-membered ring also includes group R that may be used to connect the heterocyclic 6-membered ring to a surface, a compound or a polymer. The $X^1$, $X^2$, $X^3$, $X^4$ and R groups may independently be hydrogen, a halogen, an alkyl, an alkylene, an alkenyl, an alkynyl, an aryl, an alkoxy, an alkylcarbonyl, an alkylcarboxyl, an amido, a carboxyl, an aromatic ring or combinations thereof. In addition, each of the $X^1$, $X^2$, $X^3$, $X^4$ and R groups may themselves be individually modified and/or substituted with one or more an alkyl, an alkylene, an alkenyl, an alkynyl, an aryl, an alkoxy, an alkylcarbonyl, an alkylcarboxyl, an amido, a carboxyl, amine, halogen, hydrogen or an aromatic ring groups.

The present invention includes a self-decontaminating monomeric or polymeric biocidal composition having the general formula 7 below.

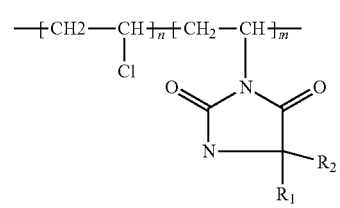

Formula 7

The composition includes an aliphatic chain attached to a heterocyclic ring. The aliphatic chain may contain a first aliphatic chain having between 1 and 40 repeats (m=1 to 40) connected to a second halogenated aliphatic chain having between 0 and 40 repeats (n=0 to 40). Alternatively, the first aliphatic chain may be halogenated or both the first aliphatic chain and the second aliphatic chain may be halogenated. Although the aliphatic chains are depicted as ethyl groups, the number of carbons, the number of bonds and the branching may vary depending on the particular application, e.g., the aliphatic chains may independently be a methyl, an ethyl, a propyl, an isopropyl, a Butyl, an isobutyl, a sec-Butyl, a tert-Butyl group and so forth. In addition, the aliphatic chains may be substituted or modified by a hydrogen, a halogen, an alkyl, an alkylene, an alkenyl, an alkynyl, an aryl, an alkoxy, an alkylcarbonyl, an alkylcarboxyl, an amido, a carboxyl, an aromatic ring or combinations thereof. The heterocyclic ring is a 5-membered ring with 2 nitrogen heteroatoms, 2 carbonyl groups and groups $R^1$ and $R^2$. groups $R^1$ and $R^2$ may be individually an alkyl, an alkylene, an alkenyl, an alkynyl, an aryl, an alkoxy, an alkylcarbonyl, an alkylcarboxyl, an amido, an amine, a halogen, a hydrogen, a carboxyl, an aromatic ring or combinations thereof. In addition, each of the $R^1$ and $R^2$ groups may themselves be individually modified and/or substituted with one or more an alkyl, an alkylene, an alkenyl, an alkynyl, an aryl, an alkoxy, an alkylcarbonyl, an alkylcarboxyl, an amido, a carboxyl or an aromatic ring groups.

The present invention includes a self-decontaminating monomeric or polymeric biocidal composition having the general formula 8 below.

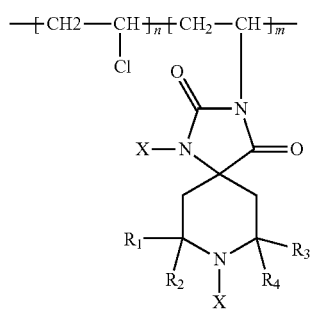

Formula 8

The composition includes an aliphatic chain attached to a bicyclic ring structure. The aliphatic chain may contain a first aliphatic chain having between 1 and 40 repeats (m=1 to 40) connected to a second halogenated aliphatic chain having between 0 and 40 repeats (n=0 to 40). Alternatively, the first aliphatic chain may be halogenated or both the first aliphatic chain and the second aliphatic chain may be halogenated. Although the aliphatic chains are depicted as ethyl groups, the number of carbons and the branching may vary depending on the particular application, e.g., the aliphatic chains may independently be a methyl, an ethyl, a propyl, an isopropyl, a Butyl, an isobutyl, a sec-Butyl, a tert-Butyl group and so forth. In addition, the aliphatic chains may be substituted or modified by a hydrogen, a halogen, an alkyl, an alkylene, an alkenyl, an alkynyl, an aryl, an alkoxy, an alkylcarbonyl, an alkylcarboxyl, an amido, a carboxyl, an aromatic ring or combinations thereof. The bicyclic ring structure (e.g., spiro rings structure sharing a common atom) includes a heterocyclic 5-membered ring and a heterocyclic 6-membered ring. The heterocyclic 5-membered ring has 2 nitrogen heteroatoms, 2 carbonyl groups. The heterocyclic 5-membered ring is attached to the aliphatic chain at one of the heteroatoms and includes group X at the other heteroatom that may be a hydrogen or a halogen. The heterocyclic 6-membered ring has a nitrogen heteroatom and groups $R^1$, $R^2$, $R^3$ and $R^4$. The nitrogen heteroatom is attached to group X that may be a hydrogen or a halogen at position. $R^1$, $R^2$, $R^3$, $R^4$ and $R^5$ may be individually be an alkyl, an alkylene, an alkenyl, an alkynyl, an aryl, an alkoxy, an alkylcarbonyl, an alkylcarboxyl, an amido, an amine, a halogen, a hydrogen, a carboxyl, an aromatic ring or combinations thereof. In addition, each of the groups may themselves individually be modified and/or substituted with one or more an alkyl, an alkylene, an alkenyl, an alkynyl, an aryl, an alkoxy, an alkylcarbonyl, an alkylcarboxyl, an amido, a carboxyl or an aromatic ring groups.

The structure may be substituted and/or modified. Although the specific examples list here contain heterocyclic 5 and 6-membered rings, the number of members to the rings, the type of heteroatoms, the location of the heteroatoms, the connection between rings, and so forth may be varied by the skilled artisan.

The present invention also provides a method of using piperidine-based N-halo-hinder amines as biofilm-controlling and photo and thermal stabilization agents. In a previous patent application by the same inventors (Sun, Y.; Chen, Z. U.S. Patent application, No. 60/640,985, pending and incorporated herein by reference), piperidine-based N-halo-hinder amines were used as antimicrobial agents.

In one example, a hindered amine light stabilizer, (e.g., bis(2,2,6,6-tetramethyl-4-piperidyl)sebacate (BTMP)) was purchased from Aldrich and recrystallized from petroleum ether. Isotactic polypropylene (e.g, PP, Aldrich) was purified by dissolution in hot o-xylene followed by precipitation with methanol.

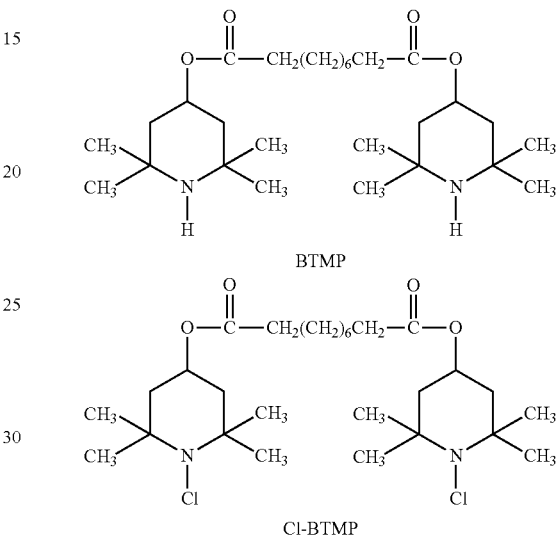

BTMP

Cl-BTMP

Preparation of bis(N-chloro-2,2,6,6-tetramethyl-4-piperidinyl)sebacate (Cl-BTMP). BTMP was submerged in about 0.6 weight percent sodium hypochlorite aqueous solutions containing about 0.05 weight percent of Triton X-100 at room temperature for 4 hours under constant stirring. The bath ratios were kept at about 1:30 and the pH values were adjusted to about 7.0 using pH buffers. After chlorination, the powders were collected, washed thoroughly with a large amount of distilled water, filtered and dried at ambient temperature under reduced pressure. After recrystallization from petroleum ether, Cl-BTMP was obtained as colorless needles.

Figure 9:
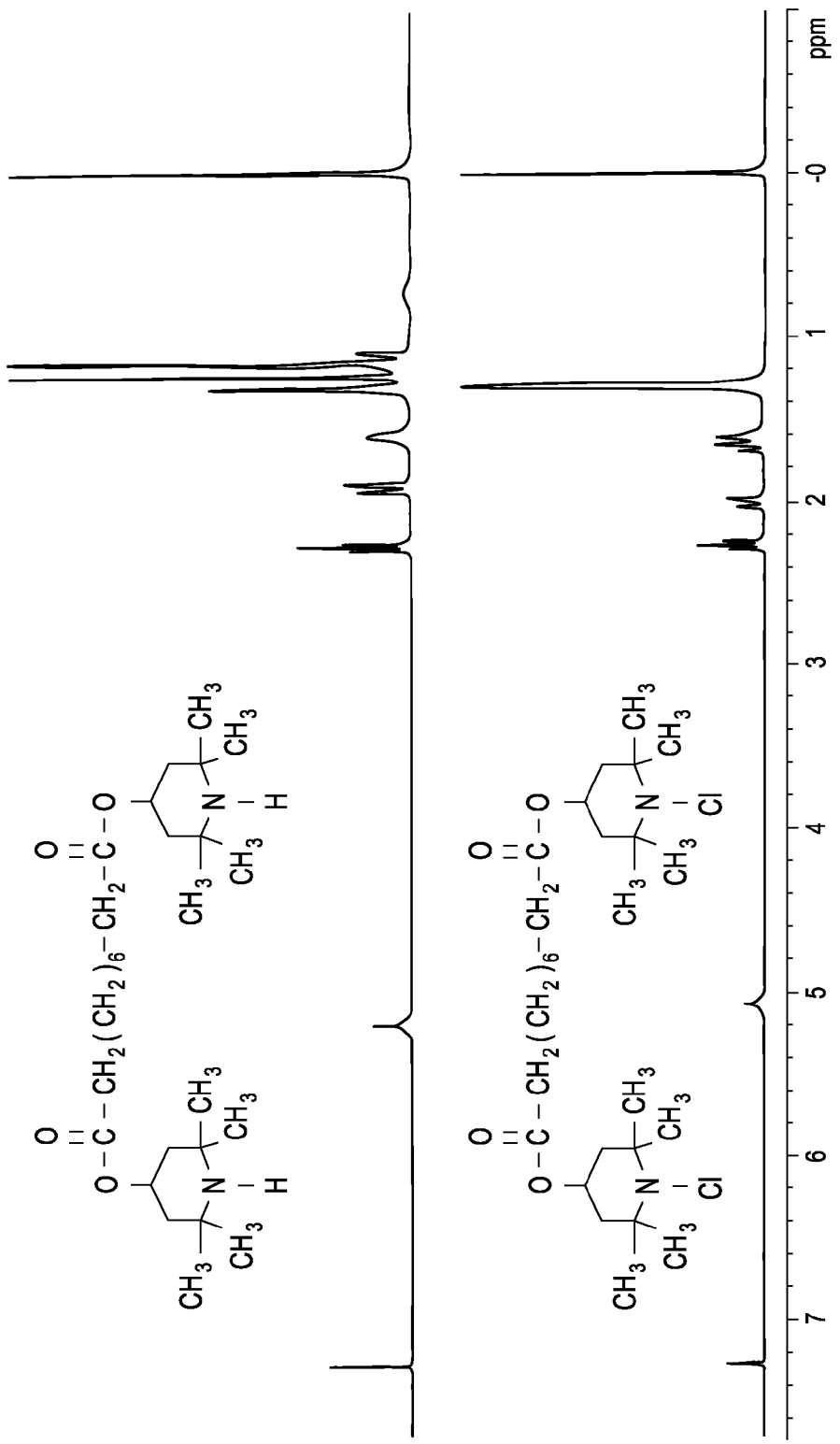
FIG. 9 is a $^1H$ NMR spectra to confirm the chemical structure of Cl-BTMP.

The structures of the N-halo hindered amines were characterized. As examples, FIG. 9 shows the $^1$H NMR spectra of the samples to confirm the chemical structure of Cl-BTMP. In the spectrum of BTMP, the amino protons showed a weak and broad peak at 0.71 ppm.[16-18] After bleach treatment, the N—H group was transformed into N—Cl structure, and the 0.71 ppm signal disappeared in the spectrum of Cl-BTMP.

Figure 10:
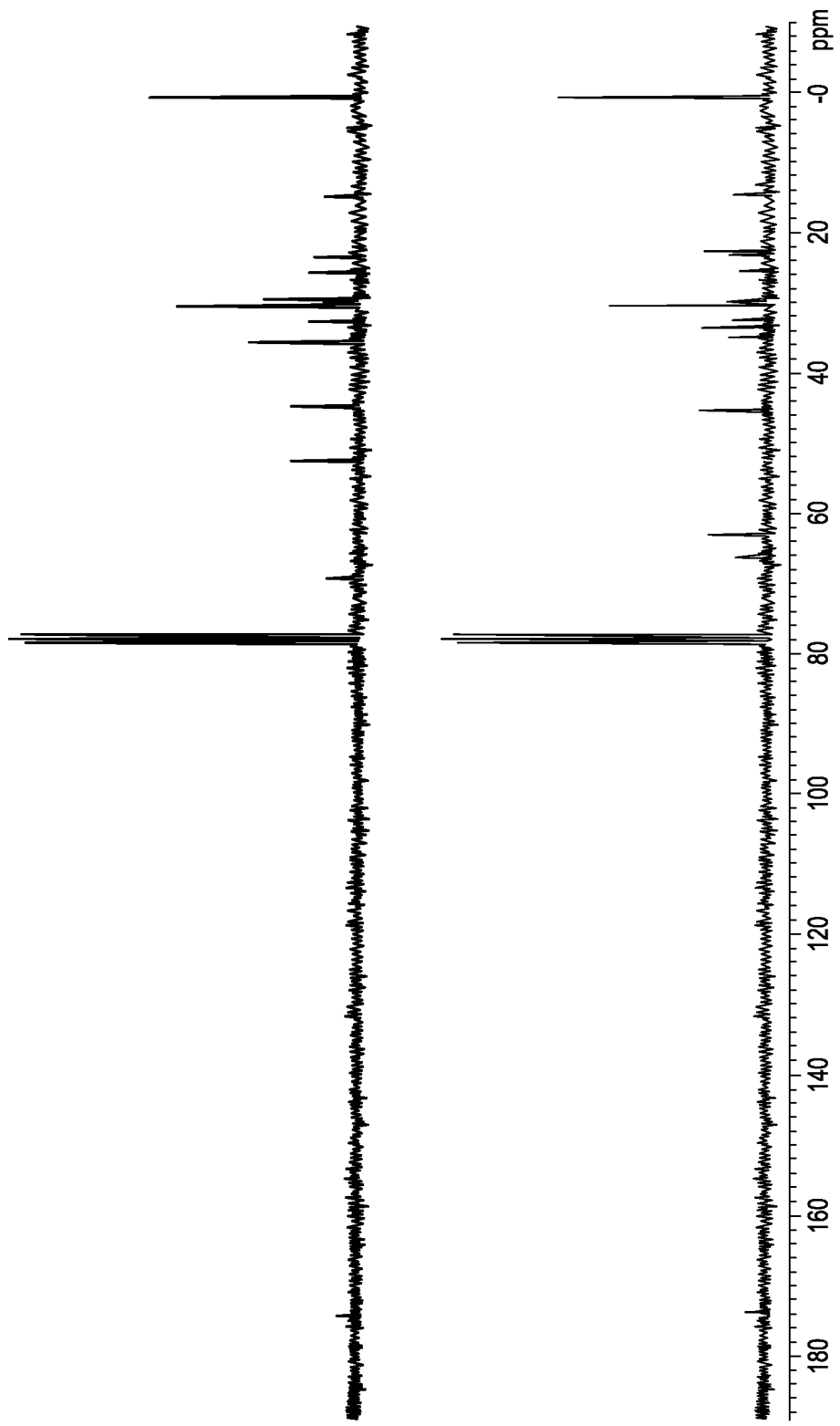
FIG. 10 is a $^{13}C$ NMR spectra to confirm the chemical structure of Cl-BTMP.

FIG. 10 shows the $^{13}$C NMR spectra of the samples to confirm the chemical structure of Cl-BTMP. Prior to chlorination, the two neighboring carbons (Ca) of the N—H group in BTMP showed a peak at 51.4 ppm, which shifted to 62.6 ppm upon bleach treatment (Ca').

Figure 11:
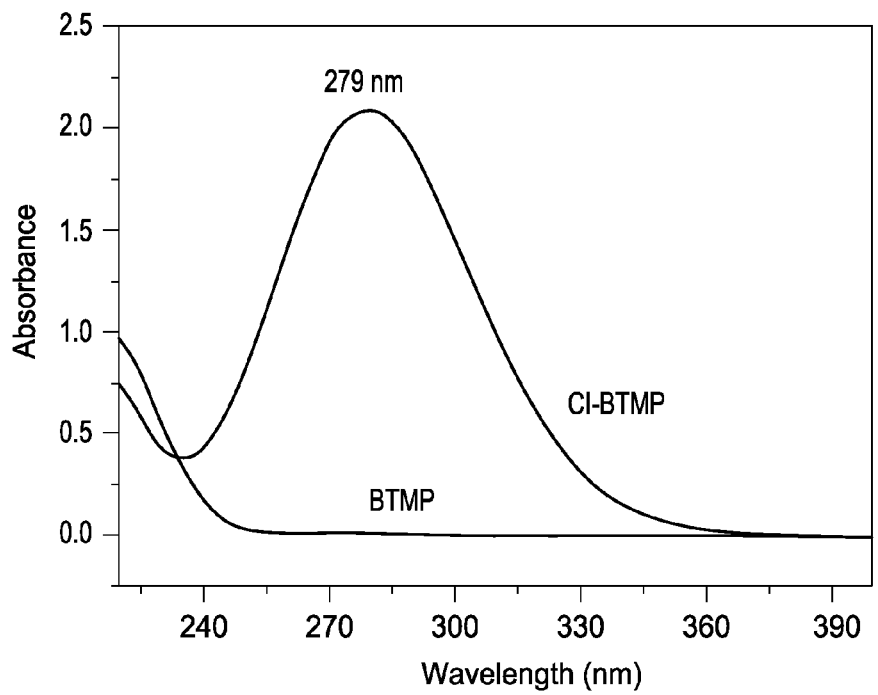
FIG. 11 is a UV/VIS spectrum to confirm the chemical structure of Cl-BTMP.

FIG. 11 is a UV/VIS spectrum of Cl-BTMP. At higher than 250 nm, BTMP did not show any absorption. However, after chlorination, a broad peak centered at 279 nm could be detected in the spectrum of Cl-BTMP.

The piperidine-based N-halo-hinder amines also show photo and thermal stabilizing effects in polymers, such as polypropylene. In one example, a predetermined amount of Cl-BTMP was added into about 5 percent PP solutions in hot o-xylene under constant stirring. After evaporation of the solvent, polymer films (e.g., thickness: about 70±5 μm) were obtained by hot pressing at about 170° C. for about 15 seconds. Chlorine contents of the resultant samples were determined by iodimetric titration. BTMP-containing PP films were prepared using the same method.

The photo stability was characterized following ASTM D 4329 Cycle A (e.g., about 8 hour UV treatment with uninsulated black panel at about 60±3° C.; about 4 hour condensation with uninsulated black panel at about 50±3° C.) using a QUA accelerated weathering tester (Q-panel products Inc., Cleveland, Ohio). The thermal stability of the samples was determined by oven aging at about 130° C. In the photo and thermal stability studies, the carbonyl index of the samples was used as a measure to evaluate the stabilizing effects of BTMP or Cl-BTMP following established methods. In the photo or thermal treatments, the FT-IR spectra of the samples were collected at different periods of time and the carbonyl index at 1713 $cm^{-1}$ was calculated according to the following equation:

$$\text{Carbonyl index} = [(\log I_0/I_t)/d] \times 100$$

where $I_0$ is the intensity of incident light, $I_t$ is the intensity of transmitted light, and d is film thickness (μm). Because the formation of carbonyl groups (e.g., ketones, carboxylic acids, and esters) is related to PP degradation, higher carbonyl index values indicate lower stabilizing effects.[14]

Figure 12A:
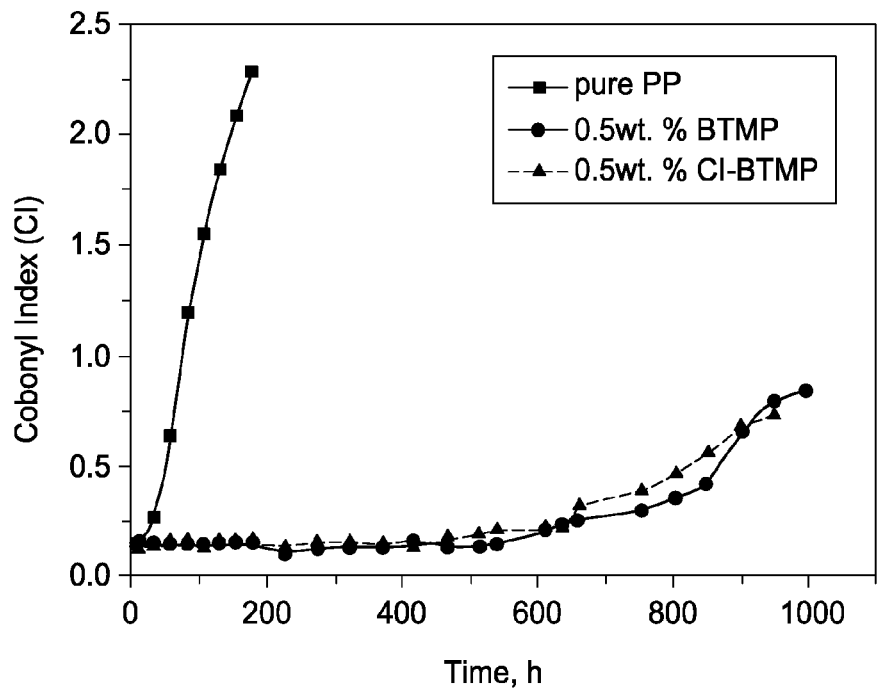
FIGS. 12A and 12B are graphs of the carbonyl index of the film samples in photo and thermal stability studies.
Figure 12B:
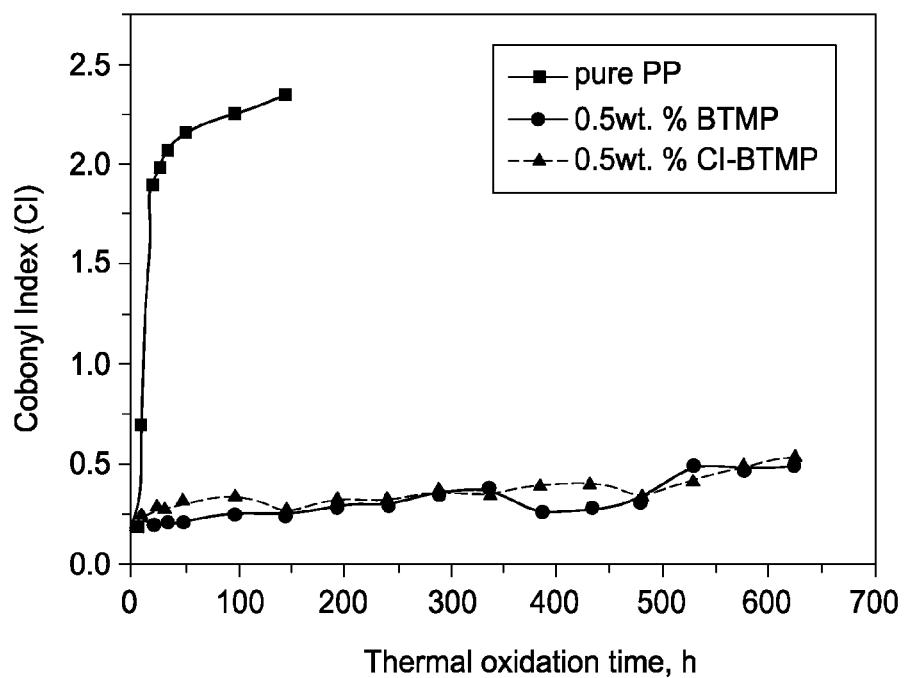

FIGS. 12A and 12B are graphs of the carbonyl index of the film samples in photo and thermal stability studies.[14c] FIG. 12A is a graph of the UV treatments showing the carbonyl index of pure PP increased rapidly, implying fast oxidization of the samples. In the presence of BTMP or Cl-BTMP, the carbonyl index of the sample was essentially unchanged up to about 600 hours of UV irradiation. Similar results were obtained in the thermal stability studies, as shown in FIG. 12B.

Figure 13A:
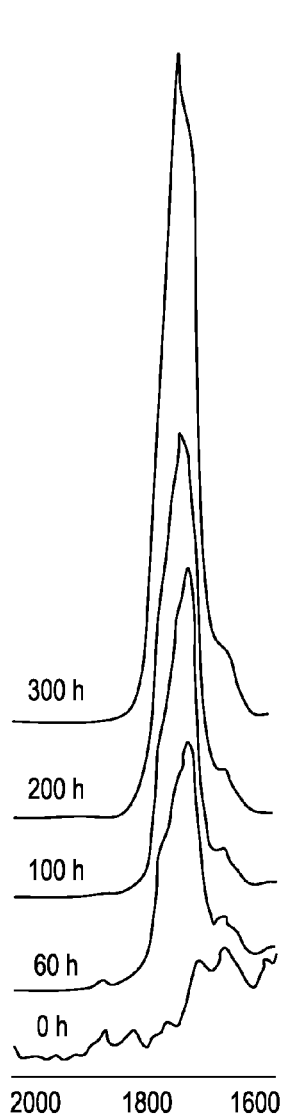
FIGS. 13A, 13B and 13C are FT-IR spectra of the samples after different periods of UV irradiation.
Figure 13B:
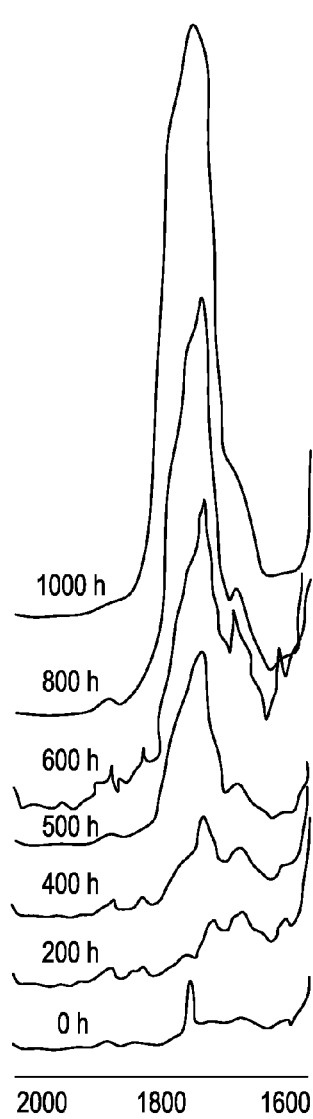
Figure 13C:
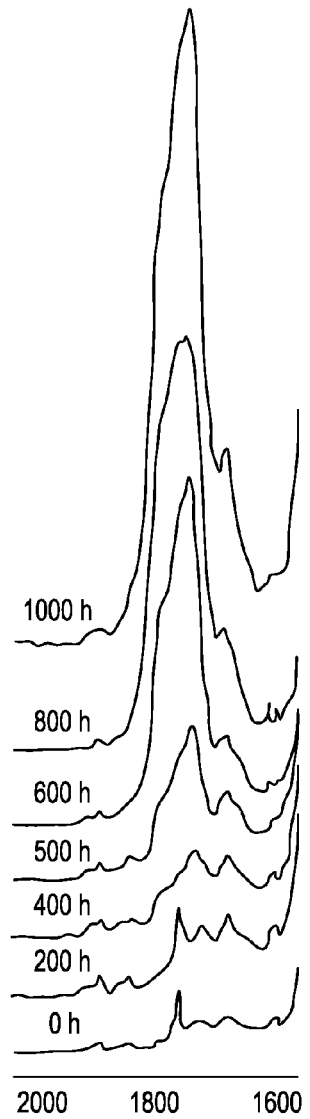

FIGS. 13A, 13B and 13C are FT-IR spectra of the samples after different periods of UV irradiation where the 1735 $cm^{-1}$ peak was caused by the carbonyl group of BTMP or Cl-BTMP. All FT-IR spectra were normalized to the $CH_3$ symmetric bend peak at 1377 $cm^{-1}$.[1,2] FIG. 13A is a FT-IR spectra of the pure PP films, while FIGS. 13B and 13C are FT-IR spectra of PP films containing about 0.5 weight percent of BTMP and Cl-BTMP respectively.

Figure 14A:
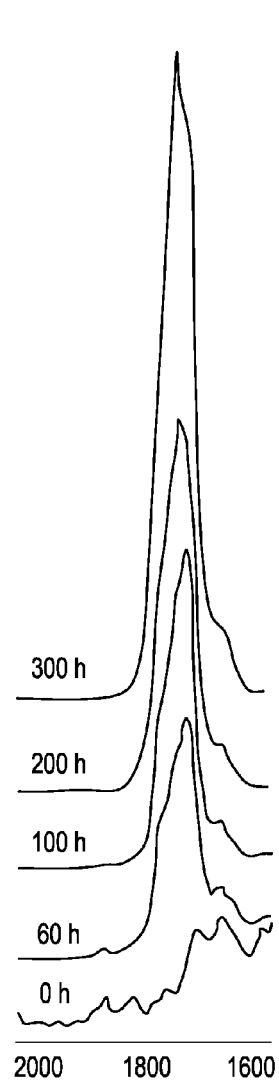
FIGS. 14A, 14B and 14C are FT-IR spectra of the samples after different periods of thermal aging at 130° C.
Figure 14B:
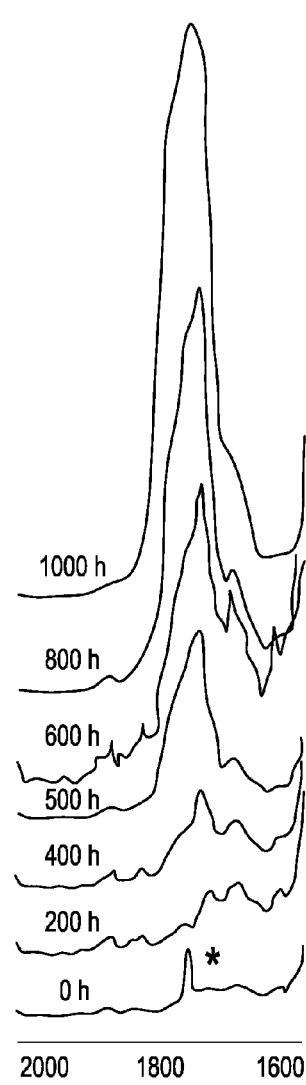
Figure 14C:
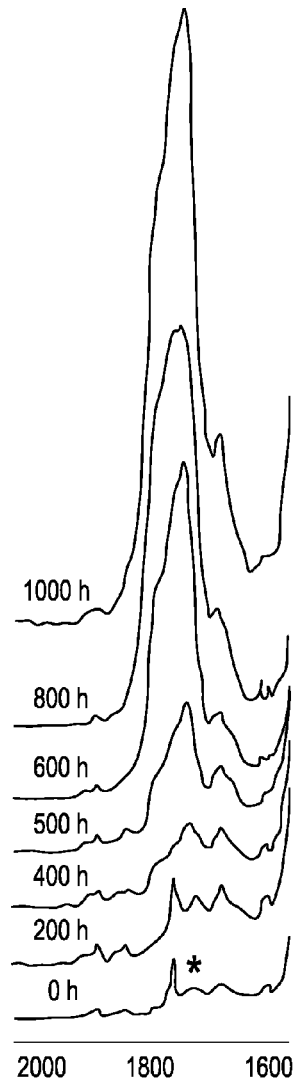
Figure 15A:
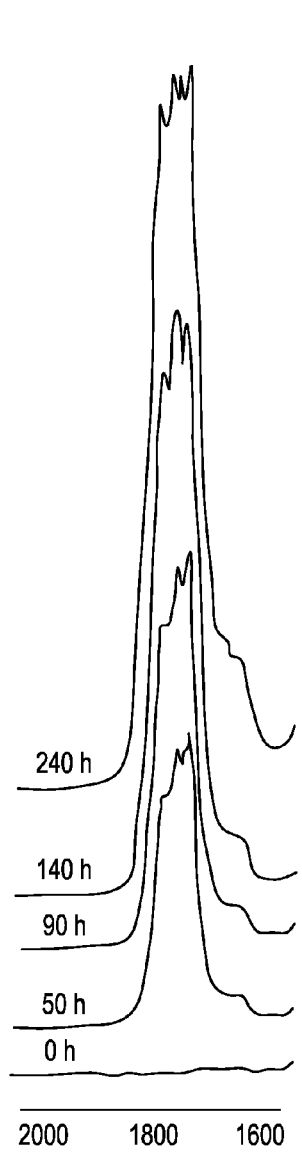
FIGS. 15A, 15B and 15C are FT-IR spectra of the samples after different periods of thermal aging at 130° C.
Figure 15B:
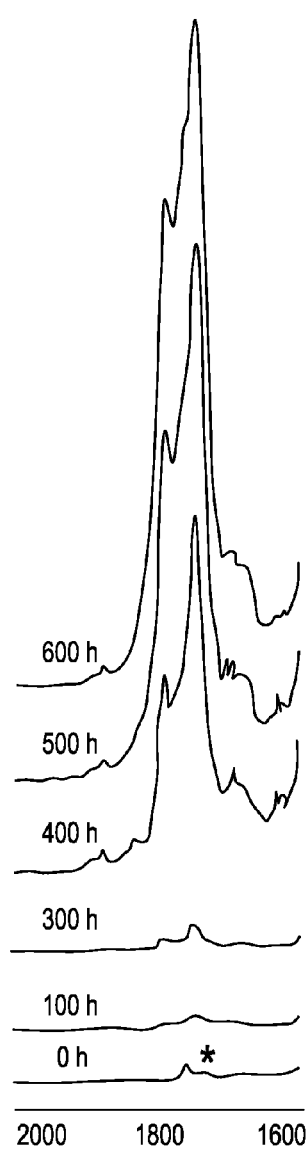
Figure 15C:
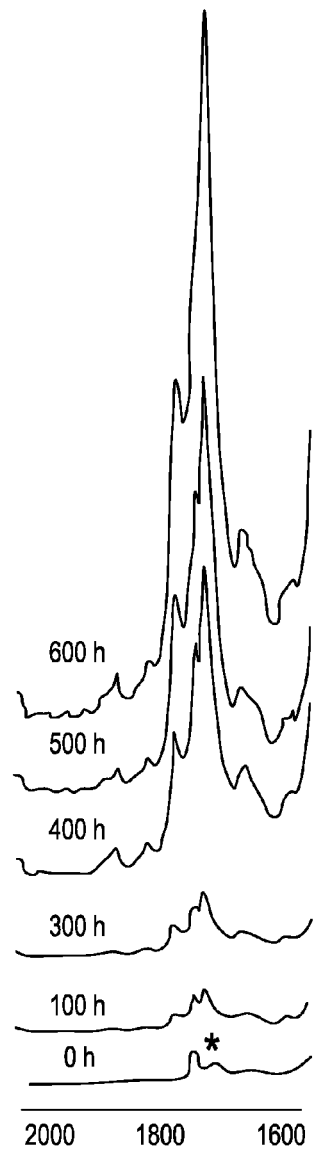

FIGS. 14A, 14B and 14C are FT-IR spectra of the samples after different periods of thermal aging at 130° C. where the 1735 $cm^{-1}$ peak was caused by the carbonyl group of BTMP or Cl-BTMP. All FT-IR spectra were normalized to the $CH_3$ symmetric bend peak at 1377 $cm^{-1}$.[27,28] FIG. 14A is a FT-IR spectra of the pure PP films, while FIGS. 14B and 14C are FT-IR spectra of PP films containing about 0.5 weight percent of BTMP and Cl-BTMP respectively. FIGS. 15A, 15B and 15C are FT-IR spectra of the samples after different periods of thermal aging. FIG. 15A is a FT-IR spectra of the pure PP films, while FIGS. 15B and 15C are FT-IR spectra of PP films containing about 0.5 weight percent of BTMP and Cl-BTMP respectively.

Figure 17:
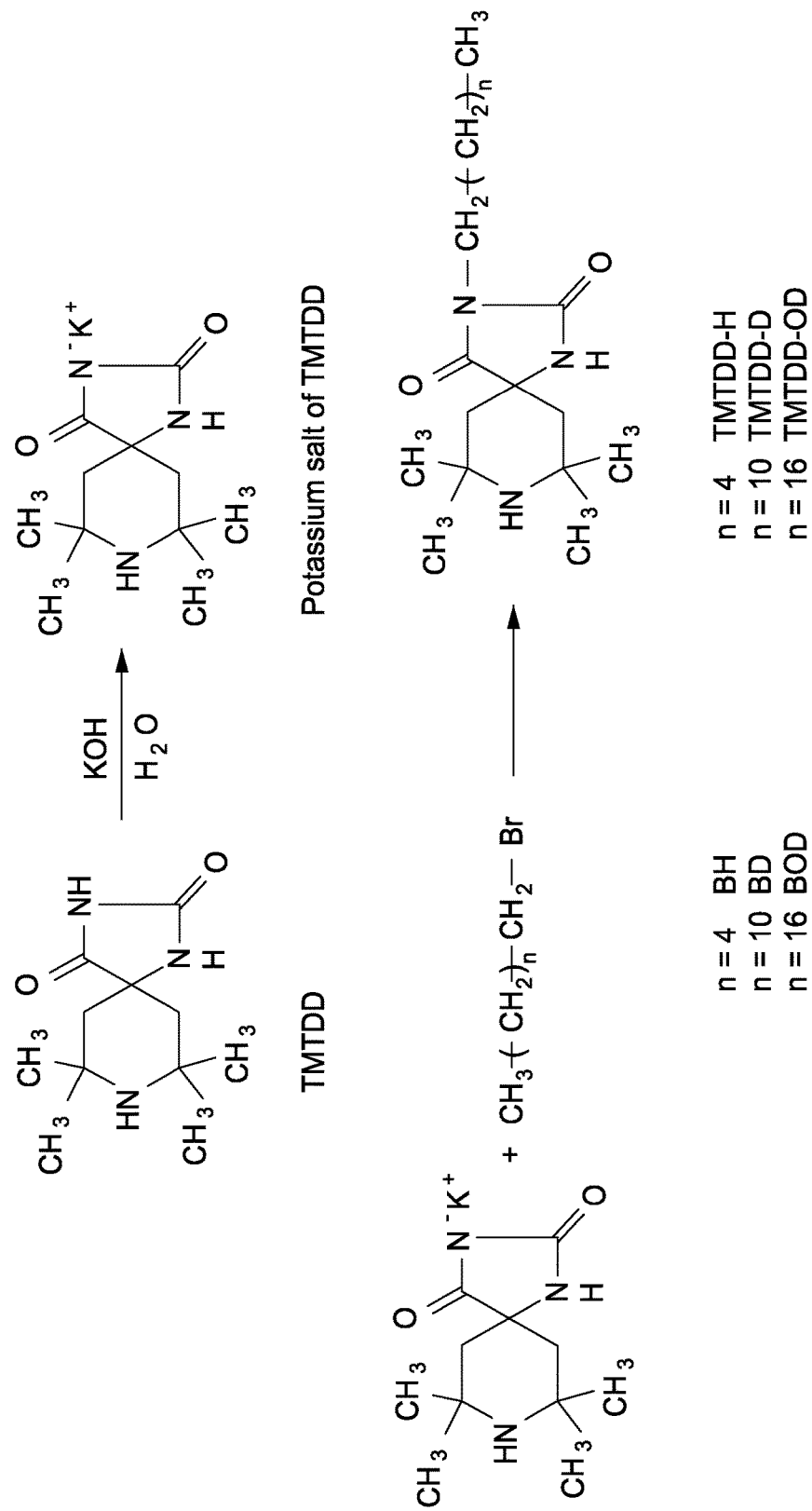
FIG. 17 is a synthesis schematic of the N-halamine compounds.

Dfs FIG. 16 is a graph of the chlorine content of Cl-BTMP after different cycles of re-chlorination treatments. FIG. 17 illustrates exemplar N-halamine compounds that may be used with the present invention. FIG. 17 indicates an aliphatic chain attached to a bicyclic ring structure. The aliphatic chain may contain between 1 and 40 repeats (n=1 to 40) with 4, 10 and 16 carbons given as an example. Although the aliphatic chain is depicted as linear group, the number of carbons and the branching may vary depending on the particular application. In addition, the aliphatic chain may be substituted or modified by a hydrogen, a halogen, an alkyl, an alkylene, an alkenyl, an alkynyl, an aryl, an alkoxy, an alkylcarbonyl, an alkylcarboxyl, an amido, a carboxyl, an aromatic ring or combinations thereof. The bicyclic ring structure (e.g., spiro rings structure sharing a common atom) includes a heterocyclic 5-membered ring and a heterocyclic 6-membered ring. The heterocyclic 5-membered ring has 2 nitrogen heteroatoms, 2 carbonyl groups. The heterocyclic 5-membered ring is attached to the aliphatic chain at one of the heteroatoms and includes group X at the other heteroatom that may be a hydrogen (or a halogen not shown). The heterocyclic 6-membered ring has a nitrogen heteroatom attached a hydrogen (or a halogen not shown).

The monomeric and polymeric N-halamine compounds of the present invention for anti-biofilm and photo and thermal stabilizing applications are compounds including sterically hindered N-halo-amine with a molecular weight higher than 200 g/mol, having the moiety of 2,2,6,6-tetramethyl-N-halo-4-piperidinyl structure, For example, in some embodiments the sterically hindered N-halo-amine is Bis(N—X-2,2,6,6-tetramethyl-4-piperidyl)sebacate; Poly[[6-[(1,1,3,3-tetramethylbutyl)amino]-s-triazine-2,4-diyl]-N—X-[(2,2,6,6-tetramethyl-4-piperidyl)imino]-hexamethylene-[(2,2,6,6-tetramethyl-4-piperidylimino]]; N—X-[(4-piperidyl)alkyl formate]; Poly[(6-morpholino-s-triazine-2,4-diyl)-N—X-[2,2,6,6-tetramethyl-4-piperidyl]imino]-hexamethylene[(2,2,6,6-tetramethyl-4-piperidyl)imino]]; 3-Dodecyl-N-chloro-(2,2,6,6-tetramethyl-4-piperidinyl)succinimide; 2,2,4,4-Tetramethyl-N—X-7-oxa-3,20-diazadispiro[5.1.11.2]-heneicosan-21-one; D-Glucitol, 1,3:2,4-bis-O—(N-chloro-2,2,6,6-tetramethyl-4-piperidinylidene); 1,1'-ethylenebis (N—X-3,3,5,5-tetramethyl-piperazinone); N—X-2,2,4,4-tetramethyl-7-oxa-20-(oxiranylmethyl)-3,20-diazadispiro [5.1.11.2]henicosan-21-one; 1,2,3,4-Butanetetracarboxylic acid, polymer with β,β,β',β'-tetramethyl-2,4,8,10-tetraoxaspiro[5.5]undecane-3,9-diethanol, N—X-2,2,6,6-tetramethyl-4-piperidinyl ester; Poly[oxy[methyl[3-[N—X-(2,2,6,6-tetramethyl4-piperidinyl)-oxy]propyl]silylene]]; 1,1',1"-[1,3,5-Triazine-2,4-6-triyltris[(cyclohexylimino)ethylene]] tris(N-chloro-3,3,5,5-tetramethyl-piperazinone); and mixtures and combinations thereof; wherein X is Cl or Br.

The present invention may be used as an additive to different materials. The present invention relates to monomeric and polymeric N-halamine having ring structures wherein 3 members of the ring are carbon, one or more members of the ring is a nitrogen or oxygen heteroatom. The compound also includes one or more chlorine, bromine or hydrogen atoms, hydroxyl, $C_1$-$C_{40}$ alkyl, benzyl, substituted benzyl, phenyl and substituted phenyl; $R^1$ to $R^{10}$ are each independently selected from the group consisting of hydrogen, $C_1$-$C_{40}$ alkyl, benzyl, substituted benzyl, phenyl and substituted phenyl. A method of using the present invention for producing a biocidal material or paint/coating through halogenation with chlorine or bromine is also disclosed. The biocidal material can be used directly, or applied as a coating or film or paint onto a plurality of substrates useful for antimicrobial and anti-biofilm properties. The biocidal properties can be regenerated by renewed halogenation in chlorine- or bromine-containing solutions. In addition to biofilm-controlling effect, the piperidine-based N-halohindered amines can also provide photo and thermal protective functions.

The novel N-halamine biocidal compounds described herein contain heterocyclic units, which have stable N—Cl or N—Br chemical bonds necessary for biocidal action. The heterocyclic N-halamine units can comprise from 4 to 7-membered rings and preferably 5 to 6-membered rings, wherein nitrogen is a heteroatom and oxygen can be a heteroatom, and which can have one or two carbonyl groups. The balance of the rings is carbon. The rings can have from three to six carbon members, from one to three nitrogen heteroatoms and 0 to 1 oxygen heteroatom. A carbon atom of these heterocyclic moieties can be joined by a linkage to an additional heterocyclic N-halamine unit by one of many possible linkages which attach to each N-halamine unit at a single non-carbonyl carbon atom, such as a lower alkyl, i.e., a three to eleven carbon chain that can be branched when greater than three carbons, or a phenyl-lower alkyl-phenyl, i.e., two phenyl groups joined by a three to 30 carbon chain that can be branched when greater than three carbons wherein one phenyl attaches to a cyclic N-halamine unit and the other phenyl attaches to a neighboring cyclic N-halamine unit. Additionally, the N-halamine units can comprise a 5- or 6-membered ring having two nitrogen heteroatoms and three (for the 5-membered ring) to four (for the 6-membered ring) carbon members, one of which can be a carbonyl group, and attaching to neighboring N-halamine units in the polymer via methylene linkages which attach to each N-halamine unit at two of the non-carbonyl carbon ring members.

In addition, the present invention provides the introduction of organic N-halamine structures into polymeric materials to provide antimicrobial functions by covalently binding N-halamine precursors (e.g., hydantoins) onto a target polymer. After halogenation, N-halalmine structures are formed in situ, and the resultant polymers provide potent antimicrobial functions against a broad range of microorganisms.

Various materials be treated using the methods of the present invention. Polymers suitable for use in the present invention include, but are not limited to, a plastic, a rubber, a textile material, a paint, a surface coating, an adhesives, cellulose, a polyester, wood pulp, paper, an absorbent, and a polyester/cellulose blend, inorganic substances such as glass, metallic and ceramic.

The polymeric plastics suitable for the present invention include thermoplastic or thermosetting resins. The thermoplastics include, but are not limited to, polyethylene, polypropylene, polystyrene and polyvinylchloride. Thermoplastics also include, polyamideimide, polyethersulfone, polyarylsulfone, polyetherimide, polyarylate, polysulfone, polycarbonate and polystyrene. Additional thermoplastics include, but are not limited to, polyetherketone, polyetheretherketone, polytetrafluoroethylene, nylon-6,6, nylon-6,12, nylon-11, nylon-12, acetal resin, polypropylene, and high and low density polyethylene.

The present invention will prevent the growth and biofilm-formation of undesirable organisms, such as the bacteria genera *Staphylococcus, Pseudomonas, Salmonella, Shigella, Legionella, Methylobacterium, Klebsiella,* and *Bacillus*; the fungi genera *Candida, Rhodoturula,* and molds such as mildew; the protozoa genera *Giardia, Entamoeba,* and *Cryptosporidium*; the viruses poliovirus, rotavirus, HIV, and herpesvirus; and the algae genera *Anabaena, Oscillatoria,* and *Chlorella*; and other sources of biofouling on surfaces. In these applications, the contents of the N-halamine compounds are in the range of between about 0.1% and about 20%.

The present invention includes a method of forming N-halamine-containing materials, which includes synthesizing the N-halamines, and adding the N-halamines to the target materials by solution blending, mechanical mixing, coating, painting, laminating and/or thermal mixing. The mixtures can be used directly or can be processed into desired articles. The present invention also includes adding precursors of the N-halamines to the target materials by solution mixing, mechanical blending, coating, painting, laminating and/or thermal mixing. The mixtures or the articles processed from the mixtures are then treated with halogen sources (e.g., chlorine bleach) to provide the antimicrobial, anti-biofilm, and/or photo and thermal stabilizing functions.

The desired functions can be lost caused by extensive uses and/or prolonged storage, in which the N-halamine structures change back to the precursors; however, because the compounds are not lost, the functions can be easily recharged by a simple exposure to halogen sources (e.g., bleach solutions).

The present invention provides a practical, flexible and cost-effective application to transform a wide range of materials into durable and rechargeable biocidal and biofilm-controlling materials, which will find wide applications in medical devices, hospital equipment, water purification/delivery systems, food storage and food packaging, hygienic products, bio-protective applications, and other related challenging environment where self-decontamination of the material is needed. In addition to biofilm-controlling, the piperidine-based N-halo-hindered amines can also provide photo and thermal stabilizing functions.

The present invention includes N-halamine biocidal composition having the formula 1, 2, 3, 4, 5, 6, 7, 8 and combinations thereof, wherein X, $X^1$, $X^2$, $X^3$ and $X^4$ are individually a Hydrogen or a halogen; $R^1$ to $R^{10}$ are independently hydrogens, halogens, one or more $C_1$ to $C_{40}$ alkyl, $C_1$ to $C_{40}$ alkylene, $C_1$ to $C_{40}$ alkenyl, $C_1$ to $C_{40}$ alkynyl, $C_1$ to $C_{40}$ aryl, $C_1$ to $C_{40}$ alkoxy, $C_1$ to $C_{40}$ alkylcarbonyl, $C_1$ to $C_{40}$ alkylcarboxyl, $C_1$ to $C_{40}$ amido, $C_1$ to $C_{40}$ carboxyl, or combinations thereof.

For example, the present invention provides a rechargeable N-halamine biocidal compound including 3-substituted-1-N-halo-5,5-disubstituted-hydantoin; 3,3'-bissubstituted-1,1'-N-halo-5,5,5'5'-substituted-2,2',4,4'-imidazolidinedione; 1,3,8-Triaza-3-substituted-7,7,9,9-substituted-1,8-N-halo-2,4-dioxospiro[4.5]decane; 3,3'-disubstituted-bis(7,7,9,9-substituted)-1,3,8-Triazaspiro[4.5]decane-1,1',8,8'N-halo-2,4-dione; 8,8'-disubstituted-bis(7,7,9,9-substituted)-1,3,8-Triazaspiro[4.5]decane-1,1',3,3'N-halo-2,4-dione; Vinyl chloride-co-3-vinyl-N-halo-5,5-disubstituted hydantoin; Vinyl chloride-co-3-vinyl-1,3,8-Triaza-7,7,9,9-substituted-1,8-N-halo-2,4-dioxospiro[4.5] decane.

The present invention also includes piperidine-based N-halo-hindered amines with a molecular weight higher than 200 g/mol, comprising the moiety of 2,2,6,6-tetramethyl-N-halo-4-piperidinyl structure, the sterically hindered N-halo-amine is selected from:

Bis(N—X-2,2,6,6-tetramethyl-4-piperidyl)sebacate;
Poly[[6-[(1,1,3,3-tetramethylbutyl)amino]-s-triazine-2,4-diyl]-N—X-[(2,2,6,6-tetramethyl-4-piperidyl)imino]-hexamethylene-[(2,2,6,6-tetramethyl-4-piperidylimino]];
N—X-[(4-piperidyl)alkyl formate];
Poly[(6-morpholino-s-triazine-2,4-diyl)-N—X-[2,2,6,6-tetramethyl-4-piperidyl]imino]-hexamethylene[(2,2,6,6-tetramethyl-4-piperidyl)imino]];
3-Dodecyl-N-chloro-(2,2,6,6-tetramethyl-4-piperidinyl) succinimide;
2,2,4,4-Tetramethyl-N—X-7-oxa-3,20-diazadispiro [5.1.11.2]-heneicosan-21-one;
D-Glucitol, 1,3:2,4-bis-O—(N-chloro-2,2,6,6-tetramethyl-4-piperidinylidene);
1,1'-ethylenebis(N—X-3,3,5,5-tetramethyl-piperazinone);

N—X-2,2,4,4-tetramethyl-7-oxa-20-(oxiranylmethyl)-3,20-diazadispiro[5.1.11.2]henicosan-21-one; 1,2,3,4-Butanetetracarboxylic acid, polymer with β,β,β',β'-tetramethyl-2,4,8,10-tetraoxaspiro[5.5]undecane-3,9-diethanol, N—X-2,2,6,6-tetramethyl-4-piperidinyl ester; Poly[oxy[methyl[3-[N—X-(2,2,6,6-tetramethyl4-piperidinyl)-oxy]propyl]silylene]]; 1,1',1"-[1,3,5-Triazine-2,4-6-triyltris[(cyclohexylimino)ethylene]]tris(N-chloro-3,3,5,5-tetramethyl-piperazinone); and mixtures and combinations thereof, wherein X is Cl or Br. The piperidine-based N-halo-hindered amines provide biofilm-controlling functions as well as photo and thermal stabilizing functions.

The present invention includes a biofilm-controlling and photo and thermal stabilizing additive having a sterically hindered N-halo-amine with a molecular weight higher than 200 g/mol. In one example, the sterically hindered N-halo-amine is a 2,2,6,6-tetramethyl-N-chloro-4-piperidinyl. In another example the sterically hindered N-halo-amine is Bis(N—X-2,2,6,6-tetramethyl-4-piperidyl)sebacate; Poly[[6-[(1,1,3,3-tetramethylbutyl)amino]-s-triazine-2,4-diyl]-N—X-[(2,2,6,6-tetramethyl-4-piperidyl)imino]-hexamethylene-[(2,2,6,6-tetramethyl-4-piperidylimino]]; N—X-[(4-piperidyl)alkyl formate]; Poly[(6-morpholino-s-triazine-2,4-diyl)-N—X-[2,2,6,6-tetramethyl-4-piperidyl]imino]-hexamethylene[(2,2,6,6-tetramethyl-4-piperidyl)imino]]; 3-Dodecyl-N-chloro-(2,2,6,6-tetramethyl-4-piperidinyl)succinimide; 2,2,4,4-Tetramethyl-N—X-7-oxa-3,20-diazadispiro[5.1.11.2]-heneicosan-21-one; D-Glucitol, 1,3:2,4-bis-O—(N-chloro-2,2,6,6-tetramethyl-4-piperidinylidene); 1,1'-ethylenebis(N—X-3,3,5,5-tetramethyl-piperazinone); N—X-2,2,4,4-tetramethyl-7-oxa-20-(oxiranylmethyl)-3,20-diazadispiro[5.1.11.2]henicosan-21-one; 1,2,3,4-Butanetetracarboxylic acid, polymer with β,β,β',β'-tetramethyl-2,4,8,10-tetraoxaspiro[5.5]undecane-3,9-diethanol, N—X-2,2,6,6-tetramethyl-4-piperidinyl ester; Poly[oxy[methyl[3-[N—X-(2,2,6,6-tetramethyl4-piperidinyl)-oxy]propyl]silylene]]; 1,1',1"-[1,3,5-Triazine-2,4-6-triyltris[(cyclohexylimino)ethylene]]tris(N-chloro-3,3,5,5-tetramethyl-piperazinone); and mixtures and combinations thereof, wherein X is Cl, Br or a combination thereof.

The present invention may be made mixed with a material prior, during or after material or article formation and provide anti-biofilm, thermal and photo stabilizing function. The material of the present invention can be subjected to extrusion, injection molding, hot pressing, coating, painting, laminating, and solvent casting, mixtures and combinations thereof and formed into a bead, a film, a tube, a sheet, a thread, a suture, a gauze, a bandage, an adhesive bandage, a vessel, a container, a cistern, a filter, a membrane, a coating, a paint and combinations thereof.

Another example of the present invention includes a hindered N-halo-amine including Bis(N—X-2,2,6,6-tetramethyl-4-piperidyl)sebacate; Poly[[6-[(1,1,3,3-tetramethylbutyl)amino]-s-triazine-2,4-diyl]-N—X-[(2,2,6,6-tetramethyl-4-piperidyl)imino]-hexamethylene-[(2,2,6,6-tetramethyl-4-piperidylimino]]; N—X-[(4-piperidyl)alkyl formate]; Poly[(6-morpholino-s-triazine-2,4-diyl)-N—X-[2,2,6,6-tetramethyl-4-piperidyl]imino]-hexamethylene[(2,2,6,6-tetramethyl-4-piperidyl)imino]]; 3-Dodecyl-N-chloro-(2,2,6,6-tetramethyl-4-piperidinyl)succinimide; 2,2,4,4-Tetramethyl-N—X-7-oxa-3,20-diazadispiro[5.1.11.2]-heneicosan-21-one; D-Glucitol, 1,3:2,4-bis-O—(N-chloro-2,2,6,6-tetramethyl-4-piperidinylidene); 1,1'-ethylenebis(N—X-3,3,5,5-tetramethyl-piperazinone); N—X-2,2,4,4-tetramethyl-7-oxa-20-(oxiranylmethyl)-3,20-diazadispiro[5.1.11.2]henicosan-21-one; 1,2,3,4-Butanetetracarboxylic acid, polymer with β,β,β',β'-tetramethyl-2,4,8,10-tetraoxaspiro[5.5]undecane-3,9-diethanol, N—X-2,2,6,6-tetramethyl-4-piperidinyl ester; Poly[oxy[methyl[3-[N—X-(2,2,6,6-tetramethyl4-piperidinyl)-oxy]propyl]silylene]]; 1,1',1"-[1,3,5-Triazine-2,4-6-triyltris[(cyclohexylimino)ethylene]]tris(N-chloro-3,3,5,5-tetramethyl-piperazinone); and mixtures and combinations thereof, wherein X is Cl, Br or combinations thereof.

The present invention includes a method of making a biofilm controlling material which is photo and thermal treatment stable by forming a N-halamine biocidal compound which is added to one or more halogen sources, wherein the N-halamine biocidal compound is transformed into one or more active N-halamine biocidal compounds. Biofilm controlling material which are stable to photo and thermal treatment may be made by mixing a sterically hindered amine light stabilizer with a source of halide atoms to form a sterically hindered N-halo-amine and forming a material in the presence of the sterically hindered N-halo-amine.

The present invention also includes a method of recharging a biofilm-controlling material, which are stable to photo and thermal challenge by exposing a sterically hindered amine stabilizer to a source of halide atoms.

In the claims, all transitional phrases such as "comprising," "including," "carrying," "having," "containing," "involving," and the like are to be understood to be open-ended, i.e., to mean including but not limited to. Only the transitional phrases "consisting of" and "consisting essentially of," respectively, shall be closed or semi-closed transitional phrases.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES (1) Zweifel, H. Plastics Additives Handbook, 5th ed.; Hanser: Munich, 2000.
(2) Edenbaum, J. Plastic additives and Modifiers Handbook; Van Norstrand Reinhold: New York, 1992.
(3) Pritchard, G. Plastic Additives; Chapman & Hall: London, 1998.
(4) Motyakin, M. V.; Schlick, S. Macromolecules 2001, 34, 2854.

(5) Kruczala, K.; Bokria, J. G.; Schlick, S. Macromolecules 2003, 36, 1909.
(6) Kruczala, K.; Varghese, B.; Bokria, J. G.; Schlick, S. Macromolecules 2003, 36, 1899.
(7) Motyakin, M. V.; Schlick, S. Macromolecules 2002, 35, 3984.
(8) Zakrzewski, J. Synth. Commun. 1988, 18, 2135.
(9) Nishimoto, S.; Chaisupakitsin, M.; Inui, T. Radiat. Phys. Chem. 1992, 39, 413.
(10) Sun, Y.; Chen, Z. U.S. Patent application, No. 60/640,985 (pending)
(11) Sun. Y.; Sun. G. Macromolecules 2002, 35, 8909.
(12) Sun, Y.; Sun, G. Ind. Eng. Chem. Res. 2004, 43, 5015.
(13). Braun, M.; Sun, Y. J. Polym. Sci. Part A: Polym. Chem. 2004, 42, 3818.
(14) (a) Setnescu, R.; Jipa, S.; Osawa, Z. Polym. Degrad. Stab. 1998, 60, 377. (b) Jansson, A.; Möller, K.; Gevert, T. Polym. Degrad. Stab. 2003, 82, 37; (c) Rabek, J. F. Photostabilization of Polymers Principles and Applications; Elsevier Applied Science: New York, 1990.
(15) Richmond J. Y.; McKinney, R. W. Biosafety in Microbiological and Biomedical Laboratories, 4th ed.; U.S. Government printing office: Washington, D.C., 1999.
(16) Lambert, J. B.; Bailey, D. S.; Michel, B. F. J. Am. Chem. Soc. 1972, 94, 3812.
(17) Booth, H.; Little, J. H. J. Chem. Soc. Perkin Trans. 2: Phys. Org. Chem. 1972, 12, 1846.
(18) Lee, C. S.; Lau, W. W. Y.; Lee, S. Y.; Goh, S. H. J. Polym. Sci. Part A: Polym. Chem. 1992, 30, 983.
(19) Metcalf, W. S. J. Chem. Soc. 1942, 48.
(20) Kleinberg, J.; Tecotzky, M.; Audrieth, L. F. Anal. Chem. 1954, 26, 1388.
(21) Czech, F. W.; Fuchs, R. J.; Antczak, H. F. Anal. Chem. 1961, 33, 705.
(22) Price, W. C. Ann. Reports 1939, 36, 47.
(23) The DSC and TGA results suggested that Cl-BTMP was thermally stable up to 200° C. See the supporting information for the thermal analysis of the samples.
(24) Kaminski, J. J.; Bodor, N.; Higuchi, T. J. Pham. Sci. 1976, 65, 553.
(25) Worley, S. D.; Williams, D. E.; Barnela, S. B. Water Res. 1987, 21, 983.
(26) Worley, S. D.; Williams, D. E. Crit. Rev. Environ. Control 1988, 18, 133.
(27) Kruczala, K.; Bokria, J. G.; Schlick, S. Macromolecules 2003, 36, 1909.
(28) Kruczala, K.; Varghese, B.; Bokria, J. G.; Schlick, S. Macromolecules 2003, 36, 1899.

What is claimed is:

1. A method of making a rechargeable antimicrobial anti-biofilm article comprising the steps of:
    adding one or more substituted hydantoins to a target material, wherein the one or more substituted hydantoins are selected from the group consisting of 1-chloro-3-ethyl-5,5-dimethylhydantoins, 1-chloro-3-dodecyl-5,5-dimethylhydantoin, 1-chloro-3-octadecyl-5,5-dimethylhydantoin, 1-chloro-3-docosyl-5,5-dimethylhydantoin, and mixtures thereof; and
    forming a rechargeable antimicrobial anti-biofilm article from the target.

2. The method of claim 1, wherein the one or more substituted hydantoins are added by solution blending, mechanical mixing, painting, coating, laminating, thermal mixing and combinations thereof.

3. The method of claim 1, further comprising the step of recharging the antimicrobial anti-biofilm article by the addition of one or more halogens.

4. The method of claim 1, wherein the target material comprises a polymer, organic material, inorganic material or combinations and mixtures thereof.

5. The method of claim 1, wherein the rechargeable antimicrobial anti-biofilm article comprises plastics, rubbers, fibers, woods, paints, coatings, nanoparticles, glass, ceramics, resins, epoxies or combinations and mixtures thereof, wherein the antimicrobial anti-biofilm article is rechargeable.

6. A method of reducing the formation of biofilms on a surface comprising the steps of:
    adding one or more substituted hydantoins to a target material, wherein the one or more substituted hydantoins comprise 1-chloro-3-ethyl-5,5-dimethylhydantoins, 1-chloro-3-dodecyl-5,5-dimethylhydantoin, 1-chloro-3-octadecyl-5,5-dimethylhydantoin, 1-chloro-3-docosyl-5,5-dimethylhydantoin and mixtures thereof; and
    processing the target material into an article to reduce the formation of biofilms on a surface of the article.

7. The method of claim 6, further comprising the step of regenerating the activity of the one or more substituted hydantoins by exposing the one or more substituted hydantoins to a halogen source.

8. The method of claim 6, wherein the article comprises plastics, rubbers, fibers, woods, paints, coatings, nanoparticles, semiconductor materials, resins, epoxies paints, stains, inorganic materials or combinations thereof.

* * * * *